(12) United States Patent
She et al.

(10) Patent No.: US 8,158,796 B2
(45) Date of Patent: Apr. 17, 2012

(54) PROCESS FOR THE PREPARATION OF RHO-KINASE INHIBITOR COMPOUNDS

(75) Inventors: Jin She, Shanghai (CN); Jonathan Bryan deCamp, Raleigh, NC (US); Paul S. Watson, Carrboro, NC (US); David J. Slade, Claremont, CA (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 301 days.

(21) Appl. No.: 12/470,377

(22) Filed: May 21, 2009

(65) Prior Publication Data

US 2010/0022775 A1   Jan. 28, 2010

Related U.S. Application Data

(60) Provisional application No. 61/073,695, filed on Jun. 18, 2008.

(51) Int. Cl.
*C07D 217/22* (2006.01)
(52) U.S. Cl. ..................................... 546/145
(58) Field of Classification Search .................. None
See application file for complete search history.

(56) References Cited

U.S. PATENT DOCUMENTS

| | | |
|---|---|---|
| 2006/0167043 A1 | 7/2006 | Iwakubo et al. |
| 2008/0021048 A1 | 1/2008 | Bennett et al. |
| 2008/0214614 A1 | 9/2008 | Lampe et al. |

FOREIGN PATENT DOCUMENTS

| | | |
|---|---|---|
| WO | WO 2005/003101 A2 | 2/2005 |
| WO | WO 2005/034866 A2 | 4/2005 |
| WO | WO 2008/077057 A2 | 6/2008 |

OTHER PUBLICATIONS

Loirand et. al., Circ Res 98:322-334 (2006).
Iwakubo, M., Takami, A., Okada, Y., Kawata, T., Tagami, Y., Sato, M., Sugiyama, T., Fukushima, K., Taya, S., Amano, M., Kaibuchi, K., and Iijima, H., (Aug. 15, 2006) Design and synthesis of rho kinase inhibitors (III). Bioorganic & Medical Chemistry, 2006, pp. 1022-1033.

*Primary Examiner* — Zinna Northington Davis
(74) *Attorney, Agent, or Firm* — Perkins Coie LLP.; Viola T. Kung

(57) ABSTRACT

The present invention is directed to practical high-yielding synthetic processes to prepare compounds of general Formula III, IV, V, VII, VIII, IX, X, XII, XIV, and XV. Such compounds are useful as final products or can be used as intermediates and be further modified to prepare other desired products such as rho-kinase inhibitors. The present invention is also directed to certain novel compounds and/or novel solid forms of certain compounds.

13 Claims, 5 Drawing Sheets

PROCESS FOR THE PREPARATION OF RHO-KINASE INHIBITOR COMPOUNDS

This application claims the benefit of U.S. Provisional Application No. 61/073,695, filed Jun. 18, 2008, which is incorporated herein by reference in its entirety.

TECHNICAL FIELD

The present invention relates generally to the synthesis of rho-associated kinase (ROCK) inhibiting compounds, salts thereof, and intermediates thereof. The invention is illustrated by the synthesis of (R)-2-(3-((3-(isoquinolin-5-ylamino)pyrrolidin-1-yl)methyl)phenoxy)ethanol, salts thereof, and intermediates thereof.

BACKGROUND OF THE INVENTION

The rho family of small GTP binding proteins can be activated by several extracellular stimuli such as growth factors, hormones and mechanic stress and function as a molecular signaling switch by cycling between an inactive GDP-bound form and an active GTP-bound form to elicit cellular responses. Rho-kinase (ROCK) functions as a key downstream mediator of Rho and exists as two isoforms (ROCK 1 and ROCK 2) that are ubiquitously expressed. ROCKs are serine/threonine kinases that regulate the function of a number of substrates including cytoskeletal proteins such as adducing, moesin, $Na^+$—$H^+$ exchanger 1 (NHE 1), LIM-kinase and vimentin, contractile proteins such as the myosin light chain phosphatase binding subunit (MYPT-1), CPI-17, myosin light chain and calponin, microtubule associated proteins such as Tau and MAP-2, neuronal growth cone associate proteins such as CRMP-2, signaling proteins such as PTEN and transcription factors such as serum response factor (Loirand et al, Circ Res 98:322-334 (2006)). ROCK is also required for cellular transformation induced by RhoA. As a key intermediary of multiple signaling pathways, ROCK regulates a diverse array of cellular phenomena including cytoskeletal rearrangement, actin stress fiber formation, proliferation, chemotaxis, cytokinesis, cytokine and chemokine secretion, endothelial or epithelial cell junction integrity, apoptosis, transcriptional activation and smooth muscle contraction. As a result of these cellular actions, ROCK regulates physiologic processes such as vasoconstriction, bronchoconstriction, tissue remodeling, inflammation, edema, platelet aggregation and proliferative disorders.

One well documented example of ROCK activity is in smooth muscle contraction. In smooth muscle cells ROCK mediates calcium sensitization and smooth muscle contraction. Agonists (noradrenaline, acetylcholine, endothelin, etc.) that bind to G protein coupled receptors produce contraction by increasing both the cytosolic $Ca^{2+}$ concentration and the $Ca^{2+}$ sensitivity of the contractile apparatus. The $Ca^{2+}$-sensitizing effect of smooth muscle constricting agents is ascribed to ROCK-mediated phosphorylation of MYPT-1, the regulatory subunit of myosin light chain phosphatase (MLCP), which inhibits the activity of MLCP resulting in enhanced phosphorylation of the myosin light chain and smooth muscle contraction (WO 2005/003101A2, WO 2005/034866A2).

Many compounds are known to have ROCK inhibition activity. Some of these compounds may not be easy to make and may require procedures that control their enantiomeric purities. There exists a need for simple and practical synthetic procedures to prepare ROCK inhibitor compounds of high chemical and enantiomeric purity.

SUMMARY OF THE INVENTION

The present invention is directed to practical high-yielding synthetic processes to prepare compounds of general Formula III, IV, V, VII, VIII, IX, X, XII, XIV, and XV. For example, a process for preparing a compound of Formula VII where upon a compound of Formula I is reacted with a compound of Formula III to provide a compound of Formula IV. A compound of Formula IV can either be chemically resolved (to give a chiral compound of Formula V which can be further reacted with a compound of Formula VI to give a compound of Formula VII) or reacted further with a compound of Formula VI to give a compound of Formula IX. Subsequently the compound of Formula IX can be chemically resolved to provide a compound of Formula X. Alternatively, a compound of Formula XI can be reacted with a compound of Formula II to provide a compound of Formula IX which can be chemically resolved to provide a compound of Formula VII. In addition, a compound of Formula XVI can be reacted with a compound of Formula II in the presence of a chiral reducing agent to give a compound of Formula XII. When no such chemical resolution is necessary due to the nature of the compound, this step can be eliminated to give a process that provides a compound of Formula XII. Such compounds are useful as final products or can be used as intermediates and be further modified to prepare other desired products. For example, such compounds are useful as rho-kinase inhibitor compounds, or are useful as intermediates for the manufacture of rho-kinase inhibitor compounds.

The present invention is also directed to (R)-2-(3-((3-(isoquinolin-5-ylamino)pyrrolidin-1-yl)methyl)phenoxy)ethanol 2,5-dihydroxybenzoic acid salt; (R)-2-(3-((3-(isoquinolin-5-ylamino)pyrrolidin-1-yl)methyl)phenoxy)ethanol 2,5-dihydroxybenzoic acid salt, in a crystalline solid form; (R)-2-(3-((3-(isoquinolin-5-ylamino)pyrrolidin-1-yl)methyl)phenoxy)ethanol L-tartaric acid salt; (R)-2-(3-((3-(isoquinolin-5-ylamino)pyrrolidin-1-yl)methyl)phenoxy)ethanol L-tartaric acid salt, in a solid form; (R)-tert-butyl 3-(isoquinolin-5-ylamino)pyrrolidine-1-carboxylate dibenzoyl-D-tartaric acid salt 2-propanol solvate; (R)-tert-butyl 3-(isoquinolin-5-ylamino)pyrrolidine-1-carboxylate dibenzoyl-D-tartaric acid salt 2-propanol solvate, in a crystalline solid form; (R)-N-(pyrrolidin-3-yl)isoquinolin-5-amine; (R)-N-(pyrrolidin-3-yl)isoquinolin-5-amine, in a crystalline solid form; (R)-N-(pyrrolidin-3-yl)isoquinolin-5-amine succinic acid salt; (R)-N-(pyrrolidin-3-yl)isoquinolin-5-amine succinic acid salt, in a crystalline solid form; (R)-N-(pyrrolidin-3-yl)isoquinolin-5-amine fumaric acid salt; (R)-N-(pyrrolidin-3-yl)isoquinolin-5-amine fumaric acid salt, in a crystalline solid form; (R)-N-(pyrrolidin-3-yl)isoquinolin-5-amine carbonic acid salt; (R)-N-(pyrrolidin-3-yl)isoquinolin-5-amine carbonic acid salt, in a crystalline solid form; (R)-2-(3-((3-(isoquinolin-5-ylamino)pyrrolidin-1-yl)methyl)phenoxy)ethyl benzoate diphosphate salt; (R)-2-(3-((3-(isoquinolin-5-ylamino)pyrrolidin-1-yl)methyl)phenoxy)ethyl benzoate diphosphate salt, in a crystalline solid form; 2-(3-formylphenoxy)ethyl benzoate; and 2-(3-formylphenoxy)ethyl benzoate, in a crystalline solid form.

DETAILED DESCRIPTION OF THE INVENTION

Definitions

Figure 1:
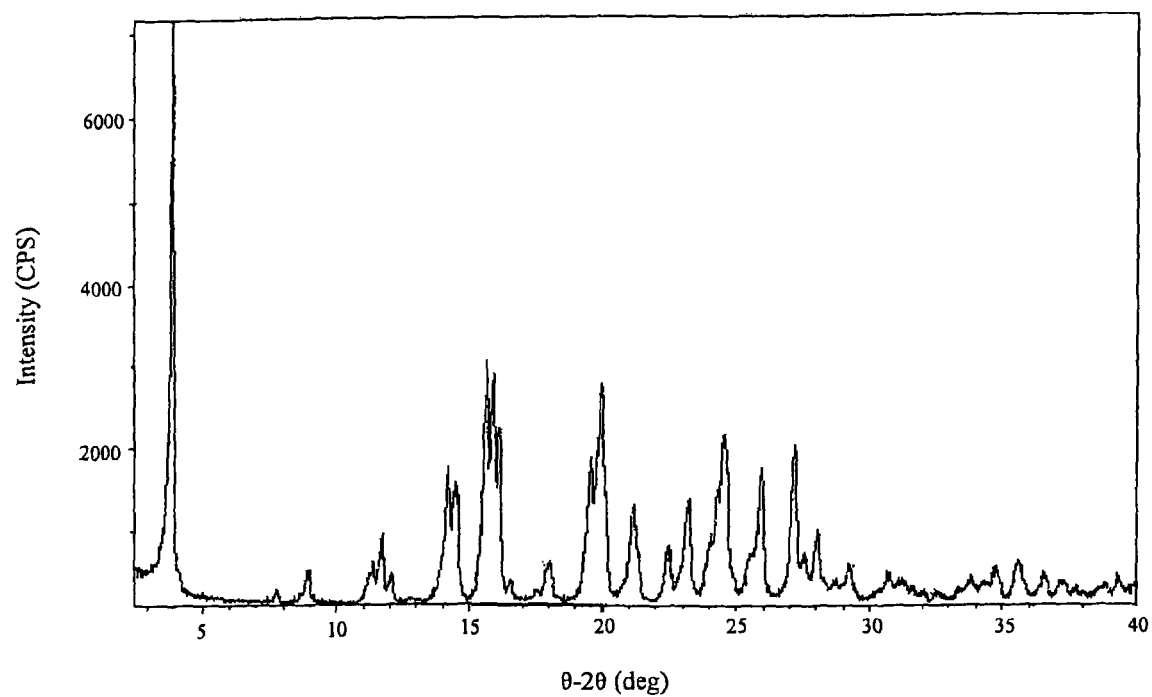
FIG. 1 shows the X-ray Powder Diffraction (XRPD) spectrogram for (R)-tert-butyl 3-(isoquinolin-5-ylamino)pyrrolidine-1-carboxylate dibenzoyl-D-tartaric acid salt, in a crystalline form.

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Alkenoxy" refers to the group alkenyl-O— wherein the alkenyl group is as defined above including optionally substituted alkenyl groups as also defined above.

"Alkynoxy" refers to the group alkynyl-O— wherein the alkynyl group is as defined above including optionally substituted alkynyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 2 to 6 carbon atoms in the alkenyl moiety and from 6 to 10 carbon atoms inclusively in the aryl moiety.

"Arylalkynyl" refers to aryl-alkynyl-groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl-groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Cycloalkylalkenyl" refers to cycloalkyl-alkenyl-groups preferably having from 2 to 6 carbon atoms inclusively in the alkenyl moiety and from 6 to 10 carbon atoms inclusively in the cycloalkyl moiety. Such cycloalkylalkenyl groups are exemplified by cyclohexylethenyl and the like.

"Cycloalkylalkynyl" refers to cycloalkyl-alkynyl-groups preferably having from 2 to 6 carbon atoms inclusively in the alkynyl moiety and from 6 to 10 carbon atoms inclusively in the cycloalkyl moiety. Such cycloalkylalkynyl groups are exemplified by cyclopropylethynyl and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl-alkenyl-groups preferably having from 2 to 6 carbon atoms inclusively in the alkenyl moiety and from 6 to 10 atoms inclusively in the heteroaryl moiety.

"Heteroarylalkynyl" refers to heteroaryl-alkynyl-groups preferably having from 2 to 6 carbon atoms inclusively in the alkynyl moiety and from 6 to 10 atoms inclusively in the heteroaryl moiety.

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl).

"Heterocycle-alkyl" refers to heterocycle-alkyl-groups preferably having from 1 to 6 carbon atoms inclusively in the alkyl moiety and from 6 to 10 atoms inclusively in the heterocycle moiety. Such heterocycle-alkyl groups are exemplified by morpholino-ethyl, pyrrolidinylmethyl, and the like.

"Heterocycle-alkenyl" refers to heterocycle-alkenyl-groups preferably having from 2 to 6 carbon atoms inclusively in the alkenyl moiety and from 6 to 10 atoms inclusively in the heterocycle moiety.

"Heterocycle-alkynyl" refers to heterocycle-alkynyl-groups preferably having from 2 to 6 carbon atoms inclusively in the alkynyl moiety and from 6 to 10 atoms inclusively in the heterocycle moiety.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, ureido, substituted ureido, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

The term "heteroatom-containing substituent" refers to substituents containing at least one non-halogen heteroatom. Examples of such substituents include, but are not limited to, hydroxy, oxo, nitro, methoxy, ethoxy, alkoxy, substituted alkoxy, trifluoromethoxy, haloalkoxy, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, ureido, substituted ureido, aryloxy, pyridyl, imidazolyl, heteroaryl, substituted heteroaryl, heteroaryloxy, heteroarylalkyl, heteroarylalkenyl, heteroarylalkynyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

"Enantiomers" are stereoisomers that are mirror images of each other and not superimposable.

"Diastereomers" are stereoisomers (isomers of identical constitution but differing three-dimensional architecture), which do not bear a mirror-image relation to each other.

A "Chiral compound" is a compound that is not superimposable on its mirror image.

"Chiral resolving agents" are optically enriched chiral acids or chiral bases that can react with a racemic or partially enantiomerically enriched base or acid to form pairs of diastereomeric salts, which can be separated by conventional techniques in physical chemistry, such as filtration or centrifugation. By selecting an appropriate enantiomer of a chiral resolving agent, either enantiomer of the substrate can be isolated as the corresponding diastereomeric salt.

"Pharmaceutically acceptable salts" are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, 2,5-dihydroxybenzoic, napthoic, oxalic, succinic, maleic, fumaric, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Tautomers" are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

"Solvates" are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definitions of compounds in Formula I to XVI encompass all possible hydrates and solvates, in any proportion, which possess the stated activity.

The inventors have unexpectedly discovered several novel processes for preparing compounds of general Formula III, IV, V, VII, VIII, IX, X, XII, XIV, and XV, which can be final products or can be used as intermediates and further modified to other desired products.

Process for Preparing a Compound of Formula VII

Scheme 1 provides the general synthesis for the compounds of Formula VII. The method comprises:

(Step 1) reacting a heterocyclic ketone (Formula I), a 5-isoquinolinyl amine (Formula II), an acid with pKa<5 (preferably with pKa of 0-2), with a reducing agent to form a compound of Formula III;

(Step 2) reacting the compound of Formula III with an acidic chiral resolving agent to form a diastereomeric salt (Formula IV);

(Step 3) reacting the diastereomeric salt with a basic aqueous solution to remove the acidic chiral resolving agent and obtain a free base of the Formula IV compound and reacting the free base of the Formula IV compound under the deprotection conditions to form a compound of Formula V; and (Step 4) reacting a compound of Formula V with a compound of Formula VI to form a compound of Formula VII.

Preparation of Formula III Compound from Formula I and II Compound (Step 1)

The present invention is directed to a process for preparing a compound of Formula III by reacting a mixture of a compound of Formula I and a compound of Formula II with a reducing agent and an acid with pKa<5 (preferably with pKa of 0-2);

Formula I

Scheme 1

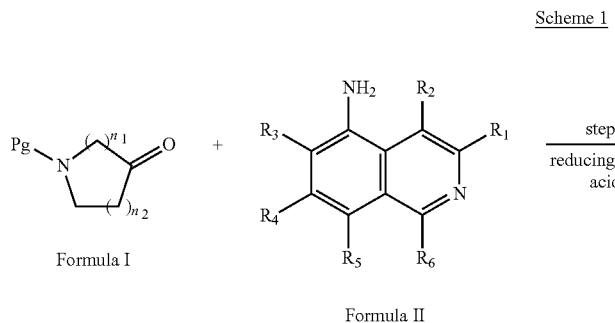

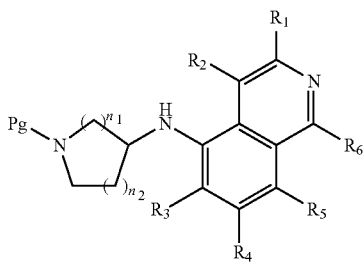

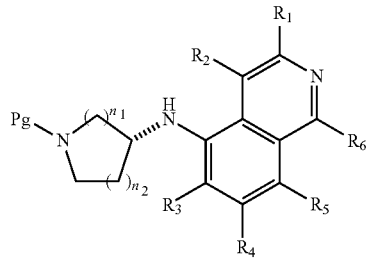

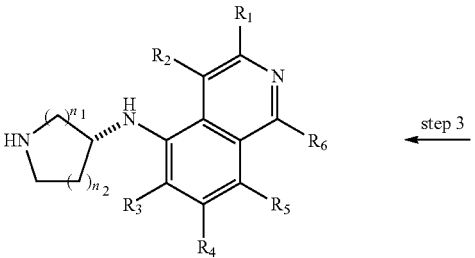

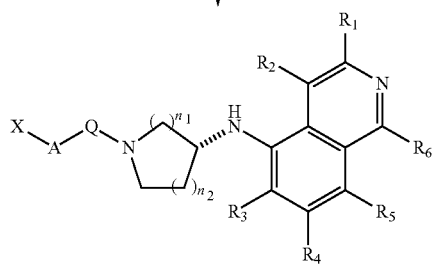

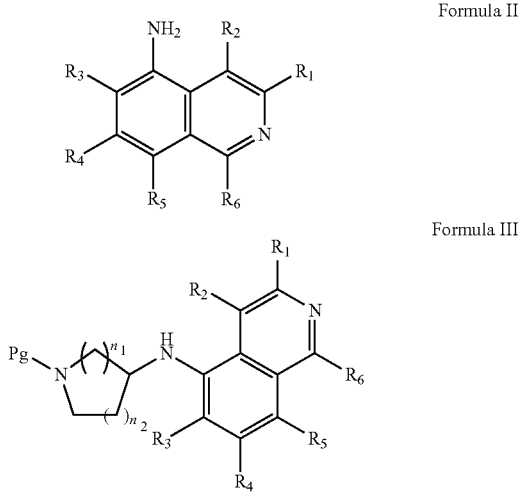

wherein Pg is a protecting group on the ring nitrogen atom; typical N-protecting groups include but are not limited to allyl, benzyl (Bn), 4-methoxybenzyl (PMB), 2,4-dimethoxybenzyl, acetyl, chloroacetyl, dichloroacetyl, trichloroacetyl, trifluoroacetyl, formyl, methylcarbamoyl, ethylcarbamoyl, 9-fluorenylmethylcarbamoyl (Fmoc), 2,2,2-trichloroethylcarbamoyl (Troc), 2-trimethylsilylethylcarbamoyl (Teoc), allylcarbamoyl (Alloc), t-butylcarbamoyl (Boc), benzylcarbamoyl (Cbz), and p-methoxybenzylcarbamoyl; the preferred N-protecting groups are benzyl (Bn), t-butylcarbamoyl (Boc), and benzylcarbamoyl (Cbz);

$n_1$ is 1 or 2;
$n_2$ is 1, 2 or 3;
provided that when $n_1$ is 2, $n_2$ is 2 or 3; and
$R_1$, $R_2$, $R_3$, $R_4$, $R_5$, and $R_6$ are independently hydrogen, halo, alkyl, alkenyl, alkynyl, amino, alkylamino, alkenylamino, alkynylamino, hydroxyl, alkoxy, alkenoxy, or alkynoxy; and preferably being H.

Preparation of Mixture A: A compound of Formula I (e.g. 1-Boc-3-pyrrolidinone), a compound of Formula II (e.g. 5-aminoisoquinoline), a suitable solvent system, and a suitable acid are charged to a vessel. The order of addition can be compelled by convenience, or by other process issues familiar to the artisan of process chemistry. However, it is preferred to charge the Formula I compound last. The amount of the Formula I compound is typically based on the molar equivalents of the Formula II compound, and is preferably 1.0-5.0 molar equivalents, more preferably 1.2-1.5 molar equivalents. Typical acids are non-aqueous inorganic and organic acids. The preferred acids are non-aqueous inorganic and organic acid with a pKa<5. The more preferred acids are non-aqueous inorganic and organic acid with a pKa between 0 to 2, such as trifluoroacetic acid and dichloroacetic acid. The amount of acid is typically based on the molar equivalents of the Formula II compound, and is preferably 1.0-20 molar equivalents, more preferably 3.0-6.0 molar equivalents if using an acid with a pKa between 0 to 2. While Mixture A can be prepared in various organic solvents except for ketones and aldehydes; the preferred solvents are tetrahydrofuran, 2-methyl-tetrahydrofuran, dichloromethane, 1,2-dichloroethane, diethyl ether, methyl tert-butyl ether, ethyl acetate, isopropyl acetate, toluene, anisole, dimethylformamide (DMF), dimethylacetamide (DMAC), acetonitrile (ACN), and acetic acid. The more preferred solvent being tetrahydrofuran, 2-methyl-tetrahydrofuran, and 1,2-dichloroethane.

Preparation of Mixture B: A reducing agent and a suitable solvent system are charged to a reaction vessel. The order of addition can be compelled by convenience, or by other process issues familiar to the artisan of process chemistry. Appropriate reducing agents include but are not limited to alkylboranes and alkylborane complexes, lithium borohydride, sodium borohydride, sodium triacetoxyborohydride, lithium cyanoborohydride, lithium triethylborohydride, sodium triethylborohydride, lithium tri-sec-butylborohydride, potassium tri-sec-butylborohydride, lithium aluminum hydride, allane, di-iso-butylaluminum hydride, potassium triphenylborohydride, sodium cyanoborohydride, trimethylsilane, hydrogen, and transfer reducing reagents. Preferred reducing reagents are sodium borohydride, sodium triacetoxyborohydride, and sodium cyanoborohydride. A more preferred reducing reagent is sodium triacetoxyborohydride. The amount of the reducing agent is typically based on the molar equivalents of the Formula II compound, and is preferably 1.0-3.0 molar equivalents, more preferably 1.2-2.0 molar equivalents. While Mixture B can be prepared in various organic solvents except for ketones and aldehydes; the preferred solvents are tetrahydrofuran, 2-methyl-tetrahydrofuran, dichloromethane, 1,2-dichloroethane, diethyl ether, methyl tert-butyl ether, ethyl acetate, isopropyl acetate, toluene, anisole, dimethylformamide (DMF), dimethylacetamide (DMAC), acetonitrile (ACN), and acetic acid. The more preferred solvent being tetrahydrofuran, 2-methyl-tetrahydrofuran, and 1,2-dichloroethane.

Either mixture can be added to the other, however it is preferred that Mixture A is then added to Mixture B. The formation of a compound of Formula III is preferably done between −20 to 50° C. The more preferred reaction temperature range is between 15 to 40° C. The reaction can be monitored by HPLC, GC or TLC. Depending on the starting solvents and temperature, the reaction is generally complete in 1-12 hours. The reaction can be quenched by the addition of an aqueous base solution. These bases include, but are not limited to inorganic bases such as sodium, lithium, and potassium carbonate; sodium, lithium, and potassium bicarbonate; and sodium, lithium and potassium hydroxide. An aqueous sodium or potassium hydroxide solution is preferred. The pH of the resulting quenched reaction is preferably above 12. The organic layer is preferably washed with more aqueous base solution followed with water. The wash is preferably performed by maintaining a temperature between 20 to 60° C. Optionally, the reaction can be further quenched by diluting it with a co-solvent; with isopropyl acetate, toluene, or methyl tert-butyl ether being preferred. The compound of Formula III is isolated, preferably by filtration or centrifugation of the organic phase. The product is preferably dried under vacuum preferably at a temperature in the range 30 to 60° C., to constant weight.

The inventors have unexpectedly discovered the above novel process that allows for preparing the Formula III compound without using a large excess of heterocyclic ketone (Formula I). Previously described methods rely on the use of a large excess (1.5-3 molar equivalents) of ketone to achieve a total consumption of 5-isoquinolinyl amine (Formula II), which not only increases the cost of the material but also adds to the difficulty of purification. The claimed process provides the product of Formula III in >80% yield (with >98% conversion of 5-isoquinolinyl amine (Formula II)) with 1.0 to 1.5 (preferably 1.2) molar equivalents of heterocyclic ketone (Formula I).

Preparation of Formula IV Compound from Formula III Compound (Step 2)

The present invention is directed to a process for preparing a diastereomeric salt (Formula IV) by reacting a compound of Formula III with an acidic chiral resolving agent or a group of acidic chiral resolving agents;

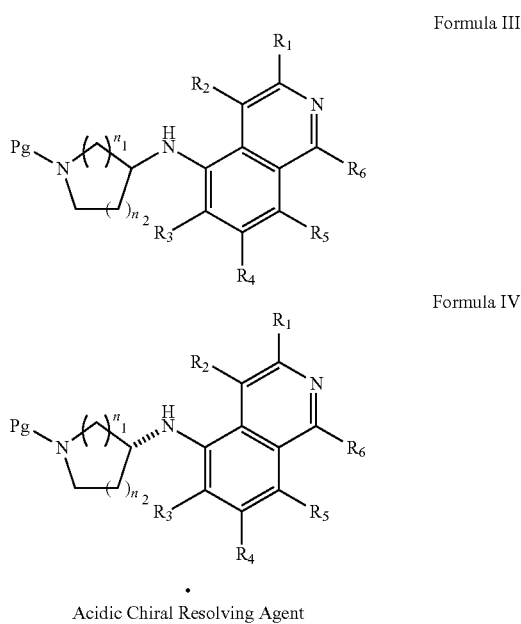

Acidic Chiral Resolving Agent wherein Pg, $R_1$-$R_6$, $n_1$ and $n_2$ are the same as described above.

The chiral resolving step is one of the key inventions of this application. In general, different enantiomers typically have different biological activities. Since different enantiomers could have different biological activities, it is important to control the chiral purity of the final compound. The present invention provides for processes that can make a final compound of the (R)- or (S)-enantiomer of the desired purity.

The inventors have unexpectedly discovered a solubility difference between two diastereomeric salts of Formula III compounds with acidic chiral resolving agents, which allows for preparing a compound of Formula IV in its diastereomerically pure form. The following process can make the diastereomeric salt of either the (R)- or (S)-enantiomer of the Formula III compound in its diastereomerically pure form by using one of the two opposite enantiomers of the chiral resolving agent in the reaction.

Chiral Resolution: A compound of Formula III (e.g. tert-Butyl 3-(isoquinolin-5-ylamino)pyrrolidine-1-carboxylate), an acidic chiral resolving agent (or a group of chiral resolving agents), and a suitable solvent system are charged to a reaction vessel. Acidic chiral resolving agents useful for this invention include (R)- or (S)-enantiomer of tartaric acid, (R)- or (S)-enantiomer of dibenzoyltartaric acid, (R)- or (S)-enantiomer of di-p-toluoyltartaric acid, (R)- or (S)-enantiomer of camphor-10-sulfonic acid, and (R)- or (S)-enantiomer of mandelic acid. (R)- or (S)-enantiomer of dibenzoyltartaric acid is preferred. The order of addition can be compelled by convenience, or by other process issues familiar to the artisan of process chemistry. Appropriate solvents include but are not limited to tetrahydrofuran, 1,3-dioxane, 1,4-dioxane, furan, ethylene glycol dimethyl ether, ethylene glycol diethyl ether, diethylene glycol dimethyl ether, diethylene glycol diethyl ether, triethylene glycol, anisole, water, methanol, ethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, acetone, N,N-dimethylpropionamide, and hexamethylphosphoramide. Preferred solvents are alcoholic solvents and a mixture of alcoholic solvents with 0-25% of water. Typical acidic chiral resolving agents include, but are not limited to both enantiomers of malic acid, tartaric acid, aspartic acid, 2-pyrrolidone-5-carboxylic acid, glutamic acid, ornithine, histidine, lysine, arginine, N-acetylglutamic acid, quinic acid, N-acetylmethionine, mandelic acid, diacetyltartaric acid, dibenzoyltartaric acid, di-p-toluoyltartaric acid, N-acetylleucine, 1-phenylethanesulfonic acid, 2-(4-hydroxyphenoxy)propionic acid, N-acetyl-3,5-dibromotyrosine, 2',4'-dichlorotartranilic acid, 4'-chlorotartranilic acid, 2'-nitrotartranilic acid, 1-phenylsuccinic acid, N-benzoylalanine, 3-bromocamphor-8-sulfonic acid, cis-camphoric acid, menthylsulfuric acid, camphor-10-sulfonic acid, N-acetylphenylalanine, N-acetyltyrosine, N-benzoylthreonine, N-carbobenzoxyalanine, N-p-toluenesulfonylaspatic acid, hydroxymethylene camphor, N-p-toluenesulfonylglutamic acid, 2,2:4,6-di-O-isopropylidine-2-keto-gulonic acid hydrate, menthoxyacetic acid, N-acetyltryptophane, 4,4',6,6'-tetranitrodiphenic acid, N-carbobenzoxyphenylalanine, benzylpenicillinnic acid, menthyl hydrogen phthalate, menthyl hydrogen succinate, and 1,1'-binaphthyl-2,2'-phosphoric acid. The preferred acidic chiral resolving agents are both enantiomers of tartaric acid, dibenzoyltartaric acid, camphor-10-sulfonic acid, di-p-toluoyltartaric acid, mandelic acid, 3-bromocamphor-8-sulfonic acid, N-acetylleucine, and malic acid. The more preferred acidic chiral resolving agents are both enantiomers of tartaric acid, dibenzoyltartaric acid, camphor-10-sulfonic acid, di-p-toluoyltartaric acid, and mandelic acid. The amount of the acidic chiral resolving agent(s) is typically based on the molar equivalents of the Formula III compound, and is preferably 0.50-1.20 molar equivalents, more preferably 0.6-0.90 molar equivalents. The amount of solvent preferably is 10-40 fold in excess of the weight of the Formula III compound. Dissolution of the solid can be facilitated by heat. The crystallization is typically facilitated by cooling. The compound of Formula IV is isolated, preferably by filtration or centrifugation of the suspension. The crude products of the Formula IV resolution can be further enantiomerically enriched by recrystallization.

Recrystallization: A crude Formula IV compound (e.g. (R)-tert-butyl 3-(isoquinolin-5-ylamino)pyrrolidine-1-carboxylate dibenzoyl-D-tartaric acid salt) and a suitable solvent system are charged to a reaction vessel. The order of addition can be compelled by convenience, or by other process issues familiar to the artisan of process chemistry. Appropriate solvents include but are not limited to tetrahydrofuran, 1,3-dioxane, 1,4-dioxane, furan, ethylene glycol dimethyl ether, ethylene glycol diethyl ether, diethylene glycol dimethyl ether, diethylene glycol diethyl ether, triethylene glycol, anisole, water, methanol, ethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, acetone, N,N-dimethylpropionamide, and hexamethylphosphoramide. Preferred solvents are alcoholic solvents and a mixture of alcoholic solvents with 0-25% of water. The amount of solvent is preferably 5-20 fold in excess of the weight of crude Formula IV compound. Dissolution of the solid can be facilitated by heat. The crystallization is preferably facilitated by cooling. The product of a Formula IV compound is isolated, preferably by filtration or centrifugation of the suspension. The product is preferably dried under vacuum preferably at a temperature in the range 30 to 60° C., to constant weight.

Preparation of Formula V Compound from Formula IV Compound (Step 3)

The present invention is directed to a process for preparing a compound of Formula V by (a) reacting the Formula IV compound with a basic aqueous solution to remove the acidic chiral resolving agent to obtain a free base of the Formula IV compound, and (b) reacting the free base of the Formula IV compound under deprotection conditions appropriate to the choice of protecting group to remove the protecting group;

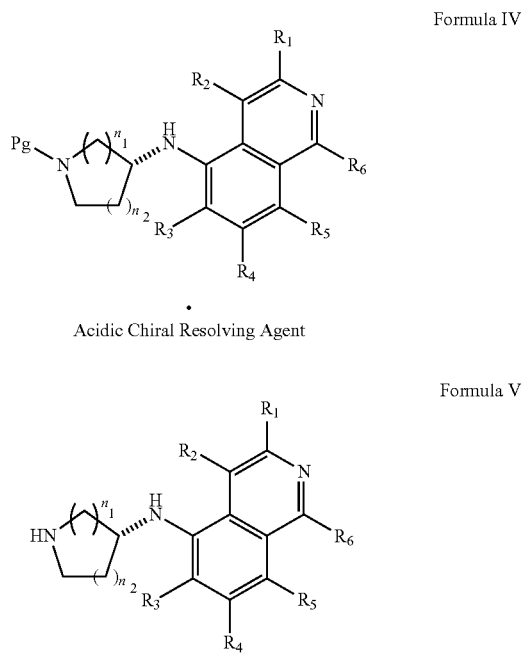

wherein Pg, $R_1$-$R_6$, $n_1$ and $n_2$ are the same as described above.

Preparation of Free Base of Formula IV compound: A compound of Formula IV (e.g. (R)-tert-butyl 3-(isoquinolin-5-ylamino)pyrrolidine-1-carboxylate dibenzoyl-D-tartaric acid salt) and a suitable solvent system are charged to a reaction vessel. The order of addition can be compelled by convenience, or by other process issues familiar to the artisan of process chemistry. Appropriate solvents include but are not limited to inert organic solvents immiscible with water. The preferred solvents are 1,2-dichloroethane, tetrahydrofuran, 2-methyltetrahydrofuran, ethyl acetate, isopropyl acetate, isobutyl acetate, tert-butyl acetate, methyl tert-butyl ether, and anisole. The more preferred solvents are isopropyl acetate and 2-methyltetrahydrofuran. The slurry is washed with a basic aqueous solution at ambient temperature (e.g., 20 to 30° C.) to remove the acidic chiral resolving agent (e.g. dibenzoyl-D-tartaric acid). These bases include, but are not limited to inorganic bases such as sodium, lithium, and potassium carbonate; and sodium, lithium and potassium hydroxide. An aqueous sodium or potassium hydroxide solution is preferred.

Preparation of Formula V compound: A compound of Formula V (e.g. (R)-N-(Pyrrolidin-3-yl)isoquinolin-5-amine) is produced by reacting the solution of the Formula IV compound free base (e.g. (R)-tert-butyl 3-(isoquinolin-5-ylamino)pyrrolidine-1-carboxylate) from the preceding procedure under deprotection conditions appropriate to the choice of protecting group. For example, when Pg is t-butylcarbamoyl (Boc), the protecting group can be removed by treating with an acid. Suitable acids include proton donors or electron pair acceptors (Lewis acids). Suitable proton donors are organic acids and inorganic acids whose pKa are about or less than 2. Suitable organic acids include methanesulfonic acid, trifluoroacetic acid, oxalic acid, benzenesulfonic acid, and p-toluenesulfonic acid. Suitable inorganic acids include hydrochloric acid, hydrobromic acid, hydroiodic acid, sulfuric acid, nitric acid, and phosphoric acid. Suitable Lewis acids include boron trifluoride, boron trichloride, zinc chloride, tin chloride, aluminum trichloride, and dimethyl bromoborane. A preferred acid is hydrochloric acid. The amount of acid is typically based on the molar equivalents of the Formula IV compound, and is preferably 2-10 molar equivalents, more preferably 3-5 molar equivalents. The formation of the Formula V compound is preferably performed between 20 to 60° C. and is typically complete within 1-48 hours. The reaction is preferably monitored by HPLC. The reaction can be quenched by the addition of an aqueous base solution. These bases include, but are not limited to inorganic bases such as sodium, lithium, and potassium carbonate; and sodium, lithium and potassium hydroxide. An aqueous sodium or potassium hydroxide solution is preferred. The pH of the resulting aqueous phase is preferably above 12. The organic and aqueous phases were separated and the aqueous layer was preferably extracted with more organic solvent. The combined organic solution of the Formula V compound is preferably dried azeotropically by distillation. The product of a Formula V compound, or a pharmaceutically acceptable salt thereof, is isolated, preferably by filtration or centrifugation of the suspension. The product is preferably dried under vacuum preferably at a temperature in the range 30 to 60° C., to constant weight.

In another example, when Pg is benzyl (Bn) or benzylcarbamoyl (Cbz), deprotection can be achieved under hydrogenolysis conditions.

Procedures to remove protecting groups are well known to a person skilled in the art, and any suitable procedures can be applied here.

Preparation of Formula VII Compound from Formula V and Formula VI Compound (Step 4)

The present invention is directed to a process for preparing a compound of Formula VII by coupling a compound of formula V with a compound of Formula VI, for example, through reductive amination or alkylation;

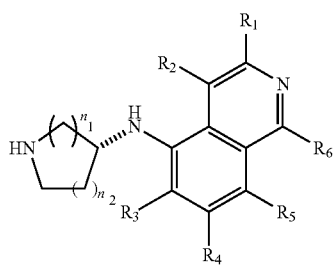

Formula V

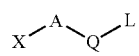

Formula VI

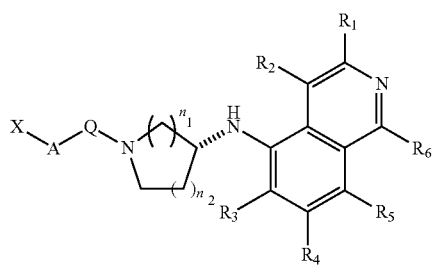

Formula VII wherein $R_1$-$R_6$, $n_1$ and $n_2$ are the same as described above;
A is aryl or heteroaryl, such as phenyl;
X is from 0 to 5 substituents on A. X as a substituent, is defined in the definition at page 7 and 8;
Q is $(CH_2)_{n3}$, $n_3$ is 0, 1 or 2;
L is the functionality that is suitable for introducing the substituent X-A-Q; preferably L is CHO, chloro, bromo, iodo, or O—$SO_2$—$R_7$ (substituted sulfonate); wherein $R_7$ is methyl, ethyl, $CF_3$, p-toluoyl, phenyl, or p-nitrophenyl.

In one embodiment, Q-L is an aldehyde $((CH_2)_{n3}CHO)$, the preferred $n_3$ is 0 or 1. The Formula VII compound is prepared from a compound of Formula V and a compound of Formula VI through reductive amination.

Reductive Amination

Preparation of Mixture C: A compound of formula V (e.g. (R)-N-(Pyrrolidin-3-yl)isoquinolin-5-amine), a compound of formula VI, and a suitable solvent system are charged to a vessel. The order of addition can be compelled by convenience, or by other process issues familiar to the artisan of process chemistry. The amount of the Formula VI compound is typically based on the molar equivalents of the compound of Formula V, and is preferably 0.7-1.3 molar equivalents, more preferably 1.0-1.1 molar equivalents. While Mixture C can be prepared in various organic solvents except for ketones and aldehydes; the preferred solvents are tetrahydrofuran, 2-methyl-tetrahydrofuran, dichloromethane, 1,2-dichloroethane, diethyl ether, methyl tert-butyl ether, ethyl acetate, isopropyl acetate, toluene, anisole, dimethylformamide (DMF), dimethylacetamide (DMAC), and acetonitrile (ACN). The more preferred solvent being tetrahydrofuran, 2-methyl-tetrahydrofuran, and 1,2-dichloroethane.

Preparation of Mixture D: A reducing agent and a suitable solvent system are charged to a reaction vessel. The order of addition can be compelled by convenience, or by other process issues familiar to the artisan of process chemistry. Appropriate reducing agents include but are not limited to alkylboranes and alkylborane complexes, lithium borohydride, sodium borohydride, sodium triacetoxyborohydride, lithium cyanoborohydride, lithium triethylborohydride, sodium triethylborohydride, lithium tri-sec-butylborohydride, potassium tri-sec-butylborohydride, lithium aluminum hydride, allane, di-iso-butylaluminum hydride, potassium triphenylborohydride, sodium cyanoborohydride, trimethylsilane, hydrogen, and transfer reducing reagents. Preferred reducing reagents are sodium borohydride, sodium triacetoxyborohydride, and sodium cyanoborohydride. A more preferred reducing reagent is sodium triacetoxyborohydride. The amount of the reducing agent is typically based on the molar equivalents of a compound of formula V, and is preferably 1.0-3.0 molar equivalents, more preferably 1.2-2.0 molar equivalents. While Mixture D can be prepared in various organic solvents except for ketones and aldehydes; the preferred solvents are tetrahydrofuran, 2-methyl-tetrahydrofuran, dichloromethane, 1,2-dichloroethane, diethyl ether, methyl tert-butyl ether, ethyl acetate, isopropyl acetate, toluene, anisole, dimethylformamide (DMF), dimethylacetamide (DMAC), and acetonitrile (ACN). The more preferred solvent being tetrahydrofuran, 2-methyl-tetrahydrofuran, and 1,2-dichloroethane.

Either mixture can be added to the other, however it is preferred that Mixture C is then added to Mixture D. The formation of a free base compound of formula VII is preferably done between −20 to 50° C. The more preferred reaction temperature range is between 15 to 35° C. The reaction can be monitored by HPLC. Depending on the starting solvents and temperature, the reaction is generally complete in 1-12 hours. The reaction can be quenched by the addition of an aqueous base solution. These bases include, but are not limited to inorganic bases such as sodium, lithium, and potassium carbonate; sodium, lithium, and potassium bicarbonate; and sodium, lithium and potassium hydroxide. An aqueous sodium or potassium carbonate solution is preferred. The pH of the resulting quenched reaction is preferably between 9 to 14. If the reaction solvent is miscible with water, an immiscible organic solvent, such as methyl tert-butyl ether, can be added to extract the formula VII product as a free base. The quench is preferably performed at ambient temperature (e.g., 20 to 30° C.). The organic layer is preferably washed with water. The product of a Formula VII compound, or a pharmaceutically acceptable salt, is isolated, preferably by filtration or centrifugation of the suspension. The product is preferably dried under vacuum preferably at a temperature in the range 30 to 60° C., to constant weight.

In another embodiment, Q-L is $(CH_2)_{n3}L$, the preferred $n_3$ is 1 or 2, the preferred L is chloro, bromo, iodo, or O—$SO_2$—$R_7$ (substituted sulfonate); wherein $R_7$ is methyl, ethyl, $CF_3$, p-tolyl, phenyl, and p-nitrophenyl. The Formula VII compound is prepared from a compound of Formula V and a compound of Formula VI through an alkylation reaction.

Alkylation

A compound of Formula V, a compound of Formula VI, a base, and a suitable solvent system are charged to a reaction vessel. The order of addition can be compelled by convenience, or by other process issues familiar to the artisan of process chemistry. The amount of the Formula VI compound is typically based on the molar equivalents of the Formula V compound, and is preferably 1.0-2.0 molar equivalents, more preferably 1.2-1.5 molar equivalents. Appropriate bases include but are not limited to inorganic bases such as sodium and potassium hydride; sodium, lithium, potassium, and cesium carbonate; and sodium, lithium and potassium hydroxide; and organic bases such as trialkylamines. The amount of the base is typically based on the molar equivalents of the Formula V compound, and is preferably 1.0-5.0 molar equivalents, more preferably 1.5-2.0 molar equivalents. The reaction can be performed in an inert organic solvent, such as tetrahydrofuran, 2-methyltetrahydrofuran, 1,4-dioxane, ethylene glycol dimethyl ether, ethylene glycol diethyl ether, diethylene glycol dimethyl ether, diethylene glycol diethyl ether, triethylene glycol diisopropyl ether, anisole, acetonitrile (ACN), dimethylformamide (DMF), dimethylacetamide (DMAC), N-methylpyrrolidinone (NMP), dimethylsulfoxide, N,N-dimethylpropionamide, and hexamethylphosphoramide. The preferred solvents are tetrahydrofuran, 2-methyltetrahydrofuran, acetonitrile (ACN), dimethylsulfoxide, dimethylformamide (DMF), dimethylacetamide (DMAC), and N-methylpyrrolidinone. The amount of the solvent is preferably 4-20 fold in excess of the weight of the Formula V compound. The formation of the Formula VII compound is performed between 0 to 80° C. A preferred reaction temperature is 20 to 40° C. The reaction is preferably monitored by HPLC. The reaction is preferably cooled to ambient temperature (e.g., 20 to 30° C.) and diluted with an inert organic solvent immiscible with water. The mixture is preferably washed with water. The solution of the Formula VII compound is then preferably dried azeotropically. The product of a Formula VII compound, or a pharmaceutically acceptable salt, is isolated, preferably by filtration or centrifugation of the suspension. The product is preferably dried under vacuum at a temperature in the range 30 to 60° C., to constant weight.

In some cases, protection of certain reactive functionalities on Formula VI is necessary to achieve some of the above transformations. In general, the need for such protecting groups as well as the conditions necessary to remove such groups from a compound of Formula VII will be apparent to those skilled in the art of organic synthesis.

The order of the steps illustrated in Scheme 1 can be changed. As illustrated in Scheme 2, alternatively, a Formula VII compound as a racemic or partially enantiomerically enriched mixture (Formula IX) can be prepared first through a sequence of a reductive amination (step 1), deprotection (step 2), and coupling with a Formula VI compound (step 3). The racemic or partially enantiomerically enriched mixture (Formula IX) is then subjected to chiral resolving conditions to form the diastereomeric salts (Formula X) with the desired stereochemistry (step 4). The enantiomerically enriched Formula VII compound can be prepared by removing the acidic resolving agent by washing with an aqueous base solution (step 5).

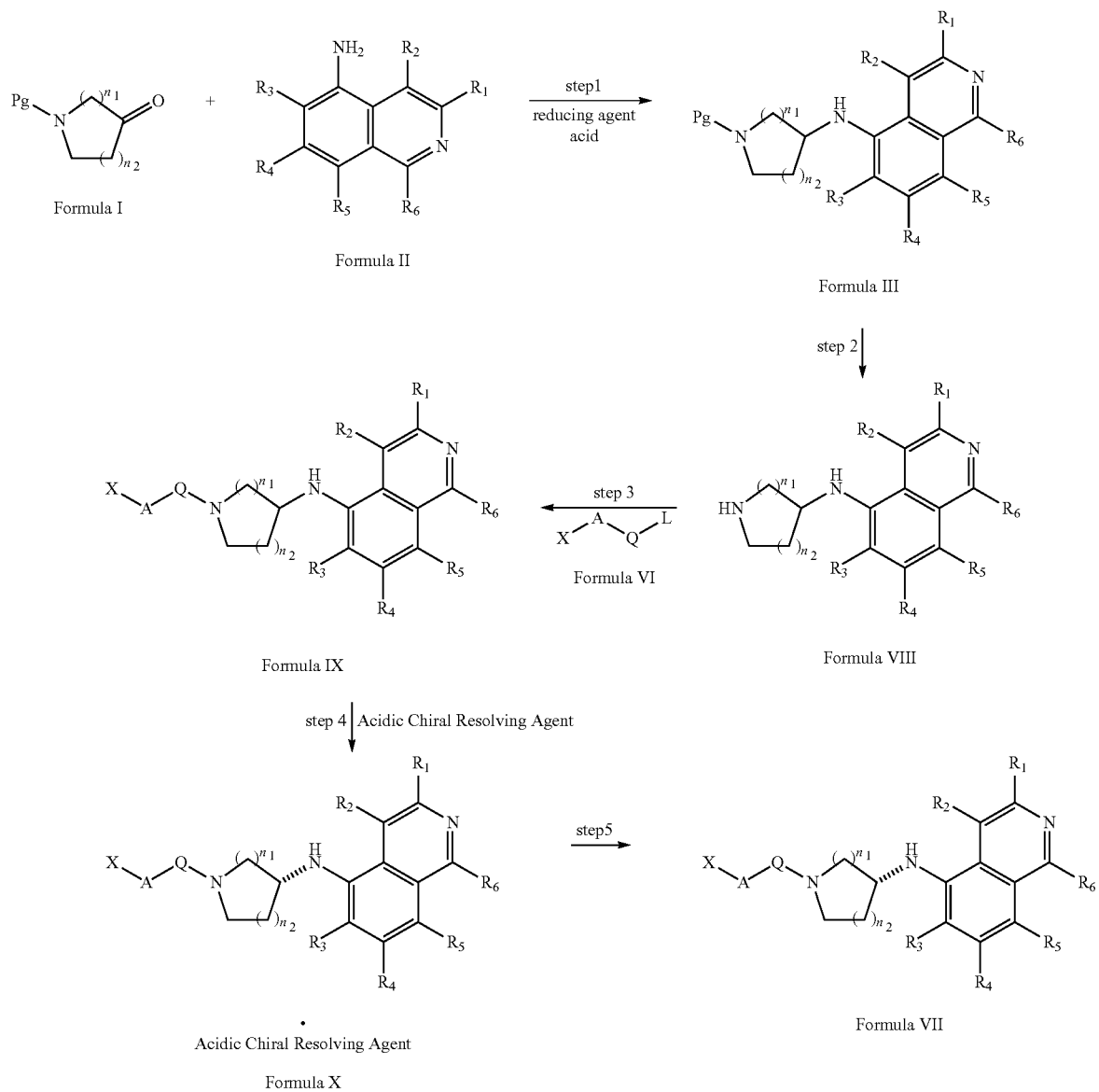

Scheme 2

As illustrated in Scheme 3, alternatively, a racemic or partially enantiomerically enriched mixture of Formula VII compounds (Formula IX) can be prepared directly from a compound of Formula XI and a compound of Formula II utilizing reductive amination conditions (step 1). The racemic or partially enantiomerically enriched mixture (Formula VIII) is then subjected to chiral resolving conditions to form the diastereomeric salts (Formula X) with the desired stereochemistry (step 2). The enantiomerically enriched Formula VII compound can be prepared by removing the acidic resolving agent by washing with an aqueous base solution (step 3).

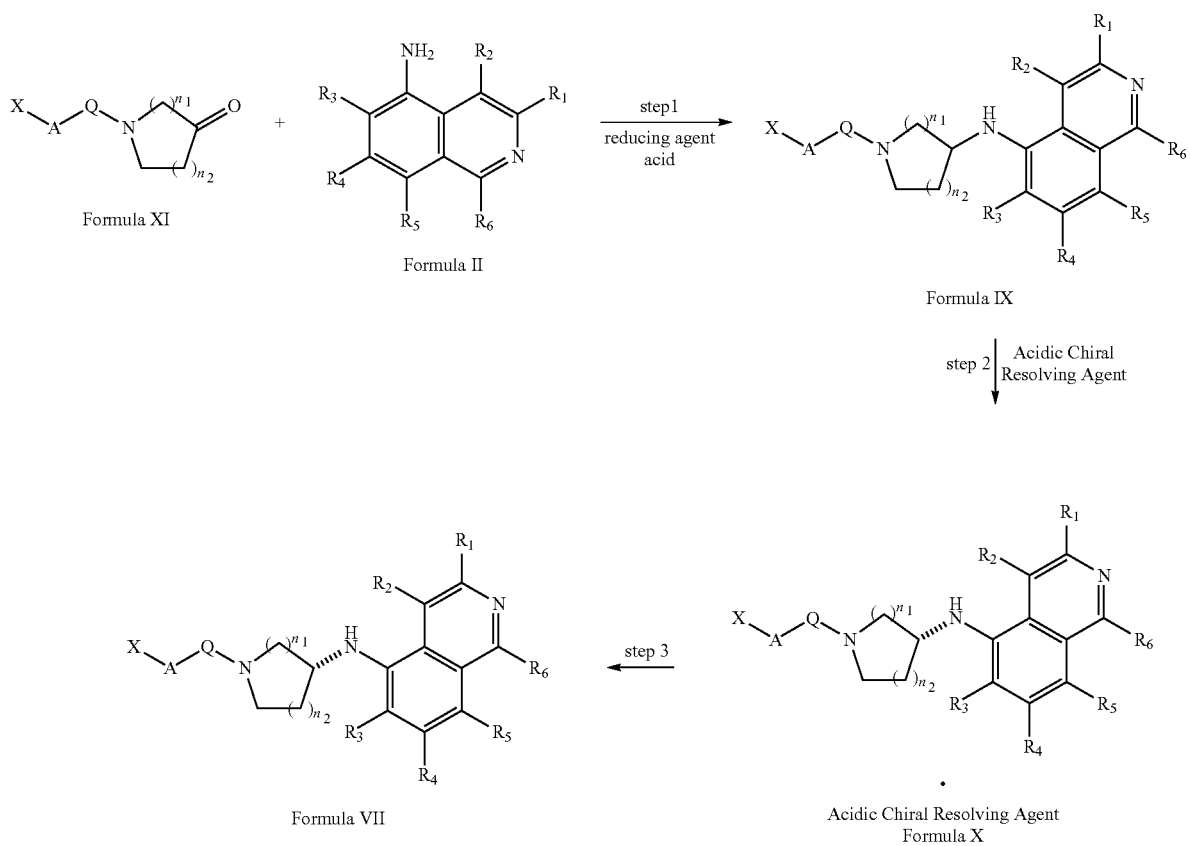

The present invention is also directed to a process for preparing a compound of Formula XII;

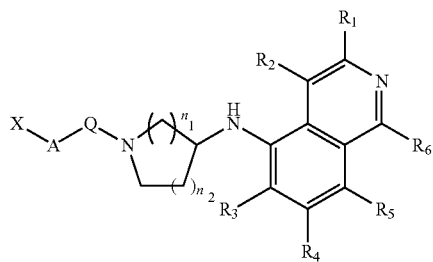

Formula XII $n_1 = 2, n_2 = 1$ or $n_1 = 3, n_2 = 2$ wherein $R_1$-$R_6$, Pg, A, X, Q, and Q-L are the same as described above;

provided that when $n_1$ is 2, $n_2$ is 1; and when $n_1$ is 3, $n_2$ is 2.

Scheme 4 describes a process of preparing compounds of Formula XII, in which the N-containing heterocycle is symmetrical. A compound of Formula XII can be prepared through a sequence of a reductive amination (step 1), deprotection (step 2), and coupling with a Formula VI compound (step 3). Alternatively, a compound of Formula XII can also be prepared through a reductive amination reaction from a compound of Formula XVI and a compound of Formula II.

Scheme 4
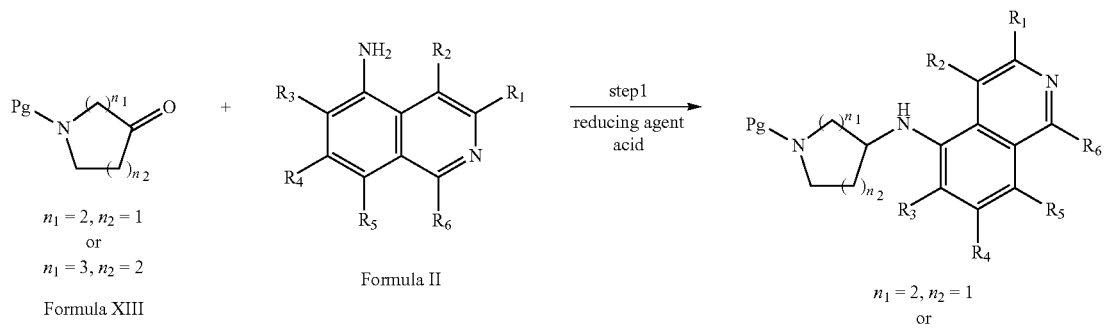
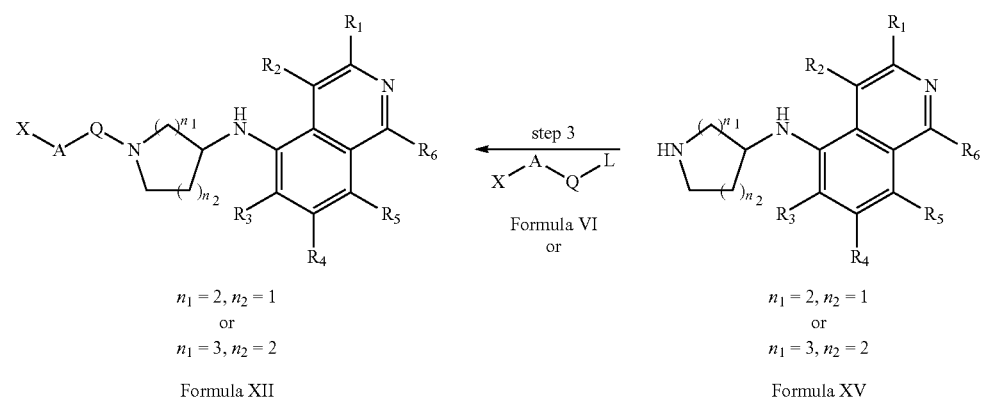
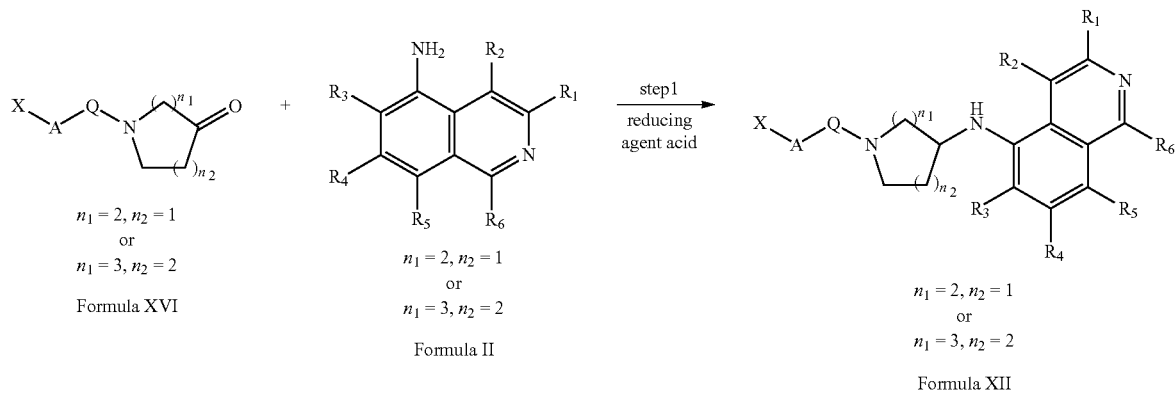
Scheme 5 provides a specific example of Scheme 1, for the preparation of (R)-2-(3-((3-(isoquinolin-5-ylamino)pyrrolidin-1-yl)methyl)phenoxy)ethanol or its salt with hydrogen chloride, L-tartaric acid, and 2,5-dihydroxybenzoic acid.

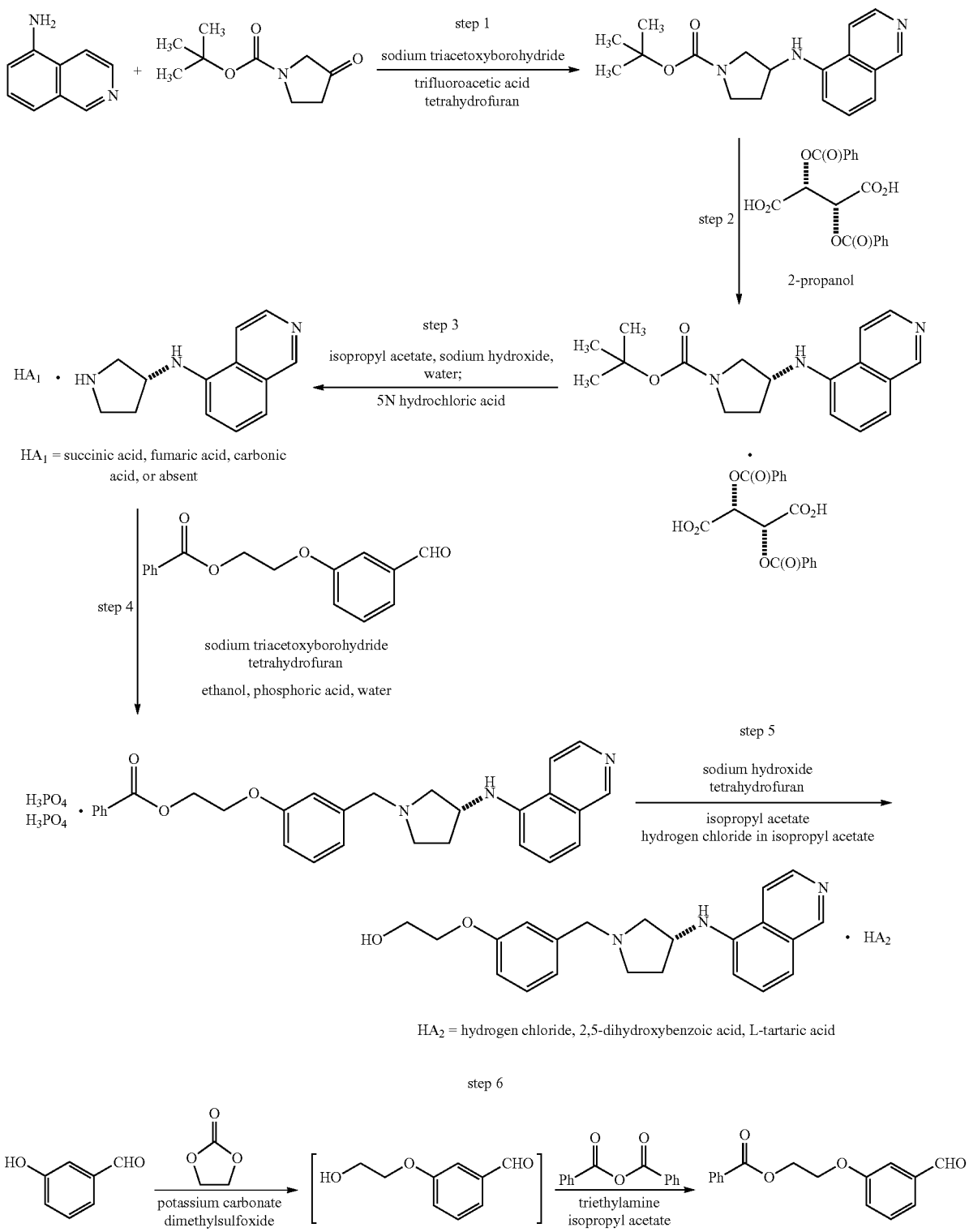

Scheme 1 to 5 are meant to be illustrative of the present invention, and are not to be taken as limiting thereof. Those having skill in the art will recognize that the starting materials can be varied and additional steps can be employed to produce compounds encompassed by the present invention. In some cases, protection of certain reactive functionalities may be necessary to achieve some of the above transformations. In general, the need for such protecting groups as well as the conditions necessary to attach and remove such groups will be apparent to those skilled in the art of organic synthesis.

Novel Compounds

The present invention provides (R)-2-(3-((3-(isoquinolin-5-ylamino)pyrrolidin-1-yl)methyl)phenoxy)ethanol 2,5-dihydroxybenzoic acid salt, preferably as a crystalline solid (a Formula VII compound).

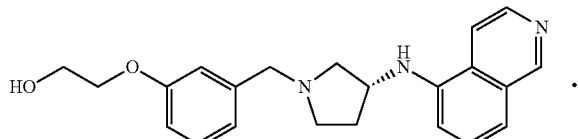

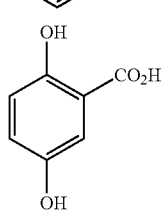

The present invention also provides (R)-2-(3-((3-(isoquinolin-5-ylamino)pyrrolidin-1-yl)methyl)phenoxy)ethanol L-tartaric acid salt, preferably as a solid (a Formula VII compound).

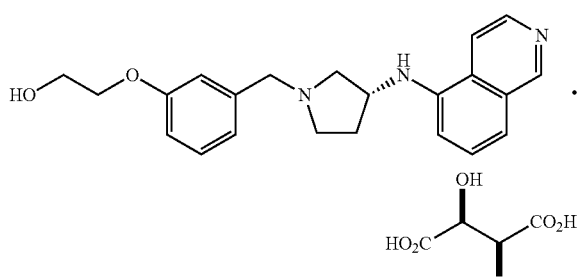

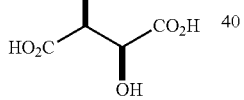

The present invention also provides (R)-tert-butyl 3-(isoquinolin-5-ylamino)pyrrolidine-1-carboxylate dibenzoyl-D-tartaric acid salt 2-propanol solvate, preferably as a crystalline solid (a Formula IV compound).

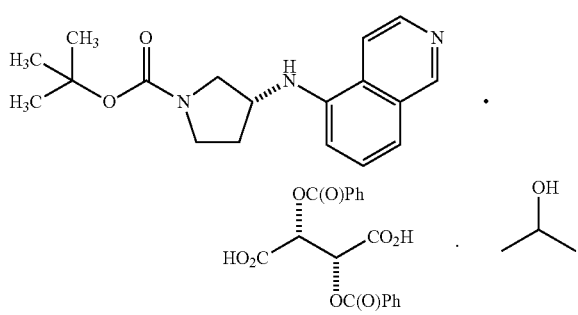

The present invention also provides (R)-N-(pyrrolidin-3-yl)isoquinolin-5-amine, preferably as a crystalline solid (a Formula V compound).

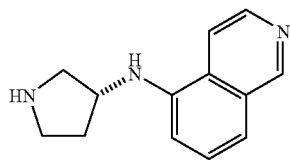

The present invention also provides (R)-N-(pyrrolidin-3-yl)isoquinolin-5-amine succinic acid salt, preferably as a crystalline solid (a Formula V compound).

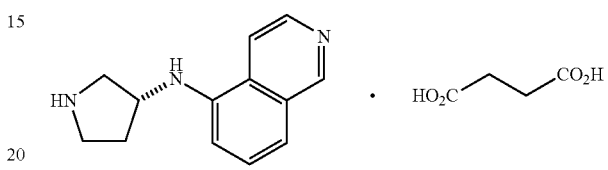

The present invention also provides (R)-N-(pyrrolidin-3-yl)isoquinolin-5-amine fumaric acid salt, preferably as a crystalline solid (a Formula V compound).

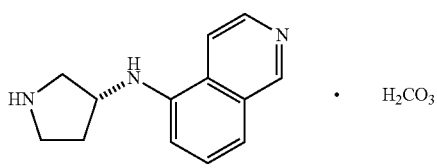

The present invention also provides (R)-N-(pyrrolidin-3-yl)isoquinolin-5-amine carbonic acid salt, preferably as a crystalline solid (a Formula V compound).

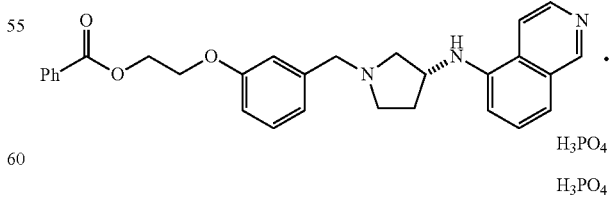

The present invention also provides (R)-2-(3-((3-(isoquinolin-5-ylamino)pyrrolidin-1-yl)methyl)phenoxy)ethyl benzoate diphosphate salt, preferably as a crystalline solid (a Formula VII compound).

The present invention also provides 2-(3-formylphenoxy)ethyl benzoate, preferably as a crystalline solid (a Formula VI compound); the preparation of the compound is illustrated in Example 13.

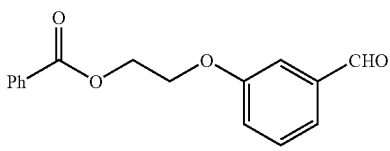

The invention is illustrated further by the following examples that are not to be construed as limiting the invention in scope to the specific procedures described in them.

EXAMPLES

Example 1

Preparation of tert-butyl 3-(isoquinolin-5-ylamino)pyrrolidine-1-carboxylate (Scheme 5, Step 1)

A 5 L flask (Flask A) equipped with a mechanical stirrer, internal temperature probe and addition funnel was charged with 5-aminoisoquinoline (300 g, 2.08 mol) and 2.7 L of tetrahydrofuran. Trifluoroacetic acid (543 mL, 7.29 mol) was added slowly while maintaining an internal temperature of <32° C. 1-Boc-3-pyrrolidinone (462.5 g, 2.50 mol) was added and the mixture was stirred for 10-30 minutes. A separate 12 L flask (Flask B) equipped with an internal temperature probe, mechanical stirrer and nitrogen inlet was flushed with nitrogen and charged with sodium triacetoxyborohydride (662.5 g, 3.13 mol) and 1.5 L of tetrahydrofuran. The contents of Flask A were slowly transferred to Flask B while maintaining an internal temperature in Flask B of <32° C. The reaction was stirred at 20-32° C. for 6 hours and all 5-aminoisoquinoline was consumed. The reaction was quenched with 3 L of 5N NaOH maintaining a temperature of <45° C. After 20 minutes, the aqueous layer was separated. The organic phase was washed with 3 L of 2N NaOH at 40° C. (with external heating). The organic phase was diluted with isopropyl acetate (2.25 L), washed with 1.5 L of water at 40° C. (with external heating), and concentrated to ~2 L by distillation. The resulting solution was cooled to ~20° C. The resulting slurry was filtered, washed (3×200 mL of MTBE), and dried in a vacuum oven at ~60° C. Approximately 536 g of tert-Butyl 3-(isoquinolin-5-ylamino)pyrrolidine-1-carboxylate was isolated as a solid (82% yield).

$^1$H NMR (DMSO-d6, 300 MHz, 60° C.) δ 9.12 (d, 1H, J=0.9 Hz), 8.40 (d, 1H, J=6.0 Hz), 8.10 (dt, 1H, J=0.9 Hz), 7.45 (t, 1H, J=7.9 Hz), 7.30 (dt, 1H, J=0.9 Hz), 6.79 (m, 1H), 6.15 (d, 1H, J=6.0 Hz), 4.19 (m, 1H), 3.69 (dd, 1H, J=10.9, 6.4 Hz), 3.30 (m, 1H, J=10.9, 4.7 Hz), 3.49 (m, 1H), 3.38 (m, 1H), 2.25 (m, 1H), 2.00 (m, 1H), 1.41 (s, 9H);
$^{13}$C NMR (DMSO-d6, 75 MHz, 60° C.) δ 151.78, 141.05, 114.79, 125.56, 142.10, 107.15, 127.86, 114.59, 128.91, 51.77, 50.57, 43.88, 30.10, 153.38, 77.96, 27.94.

Example 2

Preparation of (R)-tert-butyl 3-(isoquinolin-5-ylamino)pyrrolidine-1-carboxylate dibenzoyl-D-tartaric Acid Salt (Scheme 5, Step 2)

Salt Formation: To a 5 L flask equipped with an internal temperature probe, a heating mantle and a mechanical stirrer were added tert-butyl 3-(isoquinolin-5-ylamino)pyrrolidine-1-carboxylate (250 g, 0.798 mol, from Example 1) and 3 L of 2-propanol. The mixture was stirred and warmed to 42° C. to form a homogeneous solution. To the stirred solution was added dibenzoyl-D-tartaric acid (D-DBTA) (242.9 g, 0.678 mol) in one portion and another 0.9 L of 2-propanol. The mixture was stirred at 40° C. for 15 minutes to form a solution. The mixture was stirred at 40° C. to form a yellow slurry. The slurry was cooled to 30° C. The suspension was filtered, washed with 2×250 mL of 2-propanol and dried in a vacuum oven at ~35° C. Approximately 204.3 g of (R)-tert-butyl 3-(isoquinolin-5-ylamino)pyrrolidine-1-carboxylate dibenzoyl-D-tartaric acid salt crude product was obtained as a yellow solid (84% ee, 38% yield).

Recrystallization: To a 12 L flask equipped with an internal temperature probe, a heating mantle and a mechanical stirrer were added (R)-tert-butyl 3-(isoquinolin-5-ylamino)pyrrolidine-1-carboxylate dibenzoyl-D-tartaric acid salt crude product (80-84% ee, 500.6 g, 0.745 mol) and 5 L of 2-propanol. The mixture was stirred and heated to 75° C. to form a homogeneous solution. The solution was cooled to 30° C. and stirred at that temperature for 18 h to form a yellow slurry. The suspension was filtered, washed with 3×300 mL of 2-propanol and dried in a vacuum oven at ~35° C. Approximately 345.6 g of (R)-tert-butyl 3-(isoquinolin-5-ylamino)pyrrolidine-1-carboxylate dibenzoyl-D-tartaric acid salt product was obtained as a yellow solid (98% ee, 69% yield).

$^1$H NMR (DMSO-d6, 300 MHz, 25° C.) δ 9.14 (s, 1H), 8.41 (d, 1H, J=6.0 Hz), 8.13 (m, 1H), 8.01 (m, 4H), 7.73 (m, 2H), 7.59 (m, 4H), 7.46 (t, 1H, J=8.0 Hz), 7.31 (m, 1H), 6.80 (m, 1H), 6.20 (d, 1H, J=6.0 Hz), 5.85 (s, 2H), 4.18 (m, 1H), 3.67 (m, 1H), 3.49 (m, 1H), 3.37 (m, 1H), 3.32 (m, 1H), 2.23 (m, 1H), 2.00 (m, 1H), 1.40 (s, 9H);
$^{13}$C NMR (DMSO-d6, 75 MHz, 60° C.) δ 166.99, 164.53, 153.46, 151.66, 142.19, 140.71, 133.63, 129.15, 128.96, 128.67, 128.62, 128.07, 125.70, 115.05, 114.74, 107.39, 78.05, 71.37, 51.91, 50.64, 43.95, 30.13, 28.00.

The X-ray Powder Diffraction (XRPD) spectrogram for (R)-tert-butyl 3-(isoquinolin-5-ylamino)pyrrolidine-1-carboxylate dibenzoyl-D-tartaric acid salt is shown in FIG. 1.

Example 3

Preparation of (R)-N-(pyrrolidin-3-yl)isoquinolin-5-amine Solution (Scheme 5, Step 3)

To a 5 L flask equipped with a mechanical stirrer and an internal temperature probe were added (R)-tert-butyl 3-(isoquinolin-5-ylamino)pyrrolidine-1-carboxylate dibenzoyl-D-tartaric acid salt (180 g, 0.27 mol, from Example 2) and 2.7 L of isopropyl acetate. The suspension was stirred while 630 mL of 1N sodium hydroxide was added maintaining an internal reaction temperature below 30° C. Stirring was continued until a biphasic solution was obtained. The aqueous layer was removed and the remaining organic layer was washed with 1N sodium hydroxide (360 mL) and water (360 mL). Five normal HCl (215 mL) was added and the reaction was stirred until all (R)-tert-butyl 3-(isoquinolin-5-ylamino)pyrrolidine-1-carboxylate was consumed. The pH of the reaction was adjusted to >12 with 270 mL of 5N sodium hydroxide. The layers were separated. The pH of the aqueous layer was adjusted to >12 with 50 mL 5 N NaOH. The aqueous layer was re-extracted with 1.5 L of isopropyl acetate. The combined organic layers were concentrated to a volume of 770 mL.

Example 4

Preparation of (R)-N-(pyrrolidin-3-yl)isoquinolin-5-amine Solid (Scheme 5, Step 3)

To a 5 L flask equipped with a mechanical stirrer and an internal temperature probe were added (R)-tert-butyl 3-(isoquinolin-5-ylamino)pyrrolidine-1-carboxylate dibenzoyl-D-tartaric acid salt (150 g, 0.22 mol, from Example 2) and 2.25 L of isopropyl acetate. The suspension was stirred while 0.525 L of 1N sodium hydroxide was added maintaining an internal reaction temperature below 30° C. Stirring was continued until a biphasic solution was obtained. The aqueous layer was removed and the remaining organic layer was washed with 1N sodium hydroxide (300 mL) and water (300 mL). Five normal HCl (180 mL) was added and the reaction was stirred until all (R)-tert-butyl 3-(isoquinolin-5-ylamino) pyrrolidine-1-carboxylate was consumed. The two layers were separated. The pH of the aqueous layer was adjusted to >12 with 225 mL of 5N sodium hydroxide. The cloudy mixture was extracted with two portions of dichloromethane (2.25 L and 1.13 L). The solution was aged for 3 days for crystallization. (R)-N-(pyrrolidin-3-yl)isoquinolin-5-amine was isolated by filtration as a off-white crystalline solid (700 mg).

$^1$H NMR (CD$_3$OD, 300 MHz, 25° C.) δ9.10 (s, 1H), 8.37 (d, 1H, J=6.1 Hz), 8.06 (d, 1H, J=6.1 Hz), 7.54 (dd, 1H, J=8.2, 7.5 Hz), 7.45 (d, 1H, J=8.2 Hz), 6.91 (d, 1H, J=7.5 Hz), 4.43 (m, 1H), 3.60 (m, 2H), 3.46 (m, 2H), 2.46 (m, 1H), 2.30 (m, 1H);

$^{13}$C NMR (CD$_3$OD, 75 MHz, 25° C.) δ151.96, 141.84, 140.50, 129.84, 128.48, 127.31, 116.91, 115.43, 109.11, 52.39, 50.38, 44.47, 30.42.

Example 5

Preparation of (R)-N-(pyrrolidin-3-yl)isoquinolin-5-amine Succinic Acid Salt (Scheme 5, Step 3)

To the amine solution produced in Example 3 was added 845 mL of 0.25 M succinic acid in ethanol. The succinate salt crystallized as a fine solid. The salt was isolated by filtration and dried in a vacuum oven at 60° C. Approximately 69 g was obtained (84% yield).

$^1$H NMR (CD$_3$OD, 300 MHz) δ 9.07 (s, 1H), 8.36 (d, J=5.9 Hz, 1H), 8.06 (d, J=5.9 Hz, 1H), 7.52 (t, J=8.3 Hz, 1H), 7.40 (d, J=8.3 Hz, 1H), 6.88 (d, J=8.3 Hz, 1H), 4.47-4.38 (m, 1H), 3.65-3.50 (m, 2H), 3.49-3.38 (m, 2H), 2.51 (s, 4H), 2.49-2.36 (m, 1H), 2.32-2.19 (m, 1H).

$^{13}$C NMR (CD$_3$OD, 75 MHz) δ 178.22, 151.89, 141.92, 140.44, 129.84, 128.52, 127.23, 116.64, 115.52, 108.91, 52.35, 50.03, 44.12, 31.53, 30.37.

Figure 2:
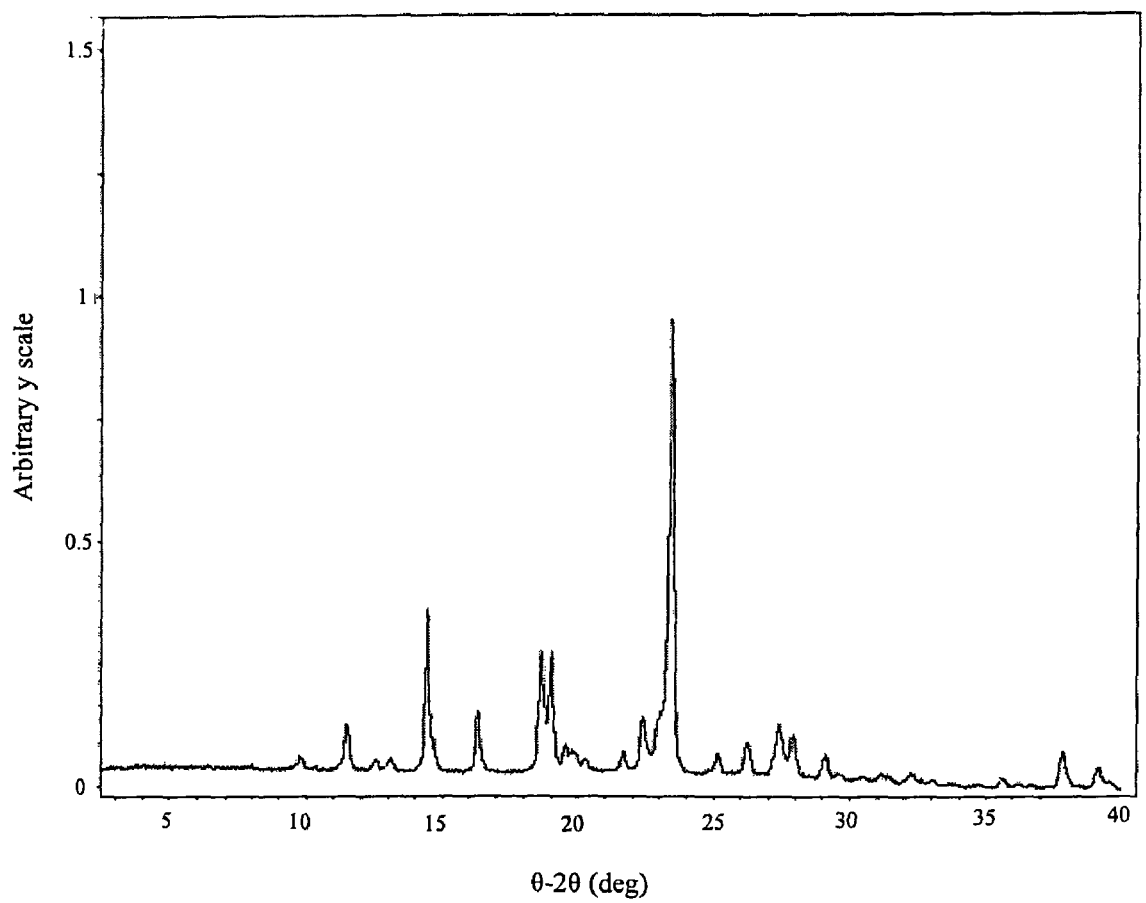
FIG. 2 shows the X-ray Powder Diffraction (XRPD) spectrogram for (R)-N-(pyrrolidin-3-yl)isoquinolin-5-amine succinic acid salt, in a crystalline form.

The X-ray Powder Diffraction (XRPD) spectrogram for (R)-N-(pyrrolidin-3-yl)isoquinolin-5-amine succinic acid salt is shown in FIG. 2.

Example 6

Preparation of (R)-N-(pyrrolidin-3-yl)isoquinolin-5-amine Fumaric Acid Salt (Scheme 5, Step 3)

To the solution of (R)-N-(pyrrolidin-3-yl)isoquinolin-5-amine in isopropyl acetate (5.0 mL, 65 mg/mL by HPLC, from Example 3) was added 6.1 mL of 0.25 M fumaric acid in ethanol. The mixture was stirred until a slurry was formed. The suspension was filtered, washed with ethanol, and dried in a vacuum oven at 60° C. (R)-N-(pyrrolidin-3-yl)isoquinolin-5-amine fumaric acid salt was obtained as a yellow solid (440 mg, 84% yield).

$^1$H NMR (CD$_3$OD, 300 MHz) δ 9.09 (s, 1H), 8.36 (d, J=5.4 Hz, 1H), 8.03 (d, J=5.4 Hz, 1H), 7.54 (t, J=7.9 Hz, 1H), 7.44 (d, J=7.9 Hz, 1H), 6.90 (d, J=7.9 Hz, 1H), 6.69 (s, 2H), 4.49-4.40 (m, 1H), 3.66-3.53 (m, 2H), 3.53-3.41 (m, 2H), 2.53-2.39 (m, 1H), 2.36-2.23 (m, 1H).

$^{13}$C NMR (CD$_3$OD, 75 MHz) δ 170.31, 151.89, 141.86, 140.40, 135.05, 129.84, 128.52, 127.30, 116.83, 115.46, 109.07, 52.35, 50.14, 44.23, 30.36.

Figure 3:
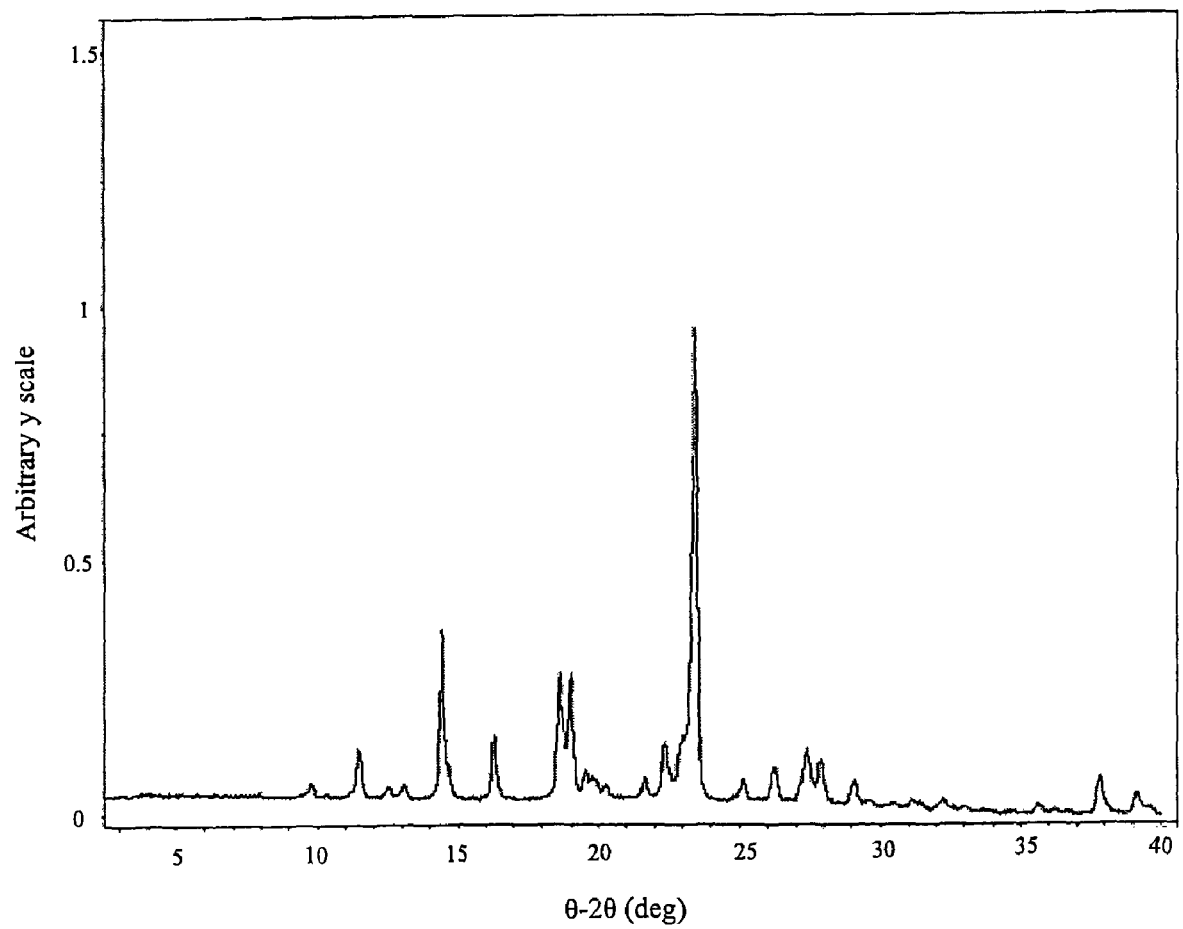
FIG. 3 shows the X-ray Powder Diffraction (XRPD) spectrogram for (R)-N-(pyrrolidin-3-yl)isoquinolin-5-amine fumaric acid salt, in a crystalline form.

The X-ray Powder Diffraction (XRPD) spectrogram for (R)-N-(pyrrolidin-3-yl)isoquinolin-5-amine fumaric acid salt is shown in FIG. 3.

Example 7

Preparation of (R)-N-(pyrrolidin-3-yl)isoquinolin-5-amine Carbonic Acid Salt (Scheme 5, Step 3)

(R)-N-(pyrrolidin-3-yl)isoquinolin-5-amine carbonate succinic acid salt (3.0 g, 9.06 mmol, from Example 5) was slurried in 100 mL of isopropyl acetate. To the slurry was added 0.5 N NaOH (50 mL) and the biphasic mixture was stirred until all solids dissolved. The aqueous layer was separated and the organic layer was washed with 50 mL of water. CO$_2$ gas was bubbled through the wet isopropyl acetate solution with stirring. The solution became light yellow and a solid began to form. After 5 minutes, the CO$_2$ source was removed and the slurry was stirred for 2 hours. The suspension was filtered and washed with 10 mL of isopropyl acetate. (R)-N-(pyrrolidin-3-yl)isoquinolin-5-amine carbonic acid salt was isolated as a solid (1.2 g).

$^1$H NMR (CD$_3$OD, 300 MHz, 50° C.) δ 9.02 (s, 1H), 8.31 (d, J=5.6 Hz, 1H), 7.97 (d, J=5.6 Hz, 1H), 7.47 (t, J=8.6 Hz, 1H), 7.32 (d, J=8.6 Hz, 1H), 6.82 (d, J=8.6 Hz, 1H), 4.28-4.15 (m, 1H), 3.43-3.21 (m, 2H), 3.20-3.07 (m, 2H), 2.39-2.24 (m, 1H), 2.07-1.94 (m, 1H).

$^{13}$C NMR (DMSO-d6, 75 MHz, 60° C.) δ 152.73, 143.28, 141.91, 129.91, 128.92, 126.51, 115.84, 115.21, 107.98, 53.71, 52.38, 45.36, 32.38.

Example 8

Preparation of (R)-2-(3-((3-(isoquinolin-5-ylamino) pyrrolidin-1-yl)methyl)phenoxy)ethyl Benzoate Diphosphate (Scheme 5, Step 4)

To a 500 mL round-bottomed flask with a magnetic stir bar were added (R)-N-(pyrrolidin-3-yl)isoquinolin-5-amine (solution/slurry in 100 mL tetrahydrofuran, 6.0 g, 28.2 mmol, from Example 3) and 2-(3-formylphenoxy)ethyl benzoate (8.00 g, 29.61 mmol, from Example 13). The mixture was stirred at 40 to 50° C. until 2-(3-formylphenoxy)ethyl benzoate is dissolved. To a 500 mL 3-necked round-bottom flask equipped with an internal temperature probe, a heating mantle and a mechanical stirrer were added sodium triacetoxyborohydride (9.57 g, 45.1 mmol) and 60 mL of dry tetrahydrofuran. The mixture was stirred at 20 to 25° C. for 15 minutes to form a white slurry. To the stirred slurry was added the pre-mixed (R)-N-(pyrrolidin-3-yl)isoquinolin-5-amine and 2-(3-formylphenoxy)ethyl benzoate in tetrahydrofuran in one portion. The mixture was stirred at 20 to 25° C. until the reaction was complete. The reaction was quenched with 110 mL of 15% Na$_2$CO$_3$ (final pH ~10). Tetrahydrofuran was removed by distillation under vacuum. The residue was extracted with 260 mL of methyl tert-butyl ether. The organic layer was washed with 260 mL of water (twice) and concentrated under reduced pressure. The residue was diluted with 264 mL of ethanol and then heated to 60° C. Phosphoric acid (0.5 M, 113 mL) was added to form a golden solution. The solution was cooled to 48 to 52° C. and seeded with 2.81 g (4.24 mmol) of (R)-2-(3-((3-(isoquinolin-5-ylamino)pyrrolidin-1-yl)methyl)phenoxy)ethyl benzoate diphosphate. The mixture was then cooled to 23 to 27° C. overnight to form a yellow slurry. The solid was isolated by filtration and washed with an additional 2×70 mL of EtOH/H$_2$O (7:3, v/v). The solid was air dried for 2 hours and then dried in a vacuum oven overnight. Approximately 11.1 g of (R)-2-(3-((3-(isoquinolin-5-ylamino)pyrrolidin-1-yl)methyl)phenoxy)ethyl benzoate diphosphate was obtained (16.7 mmol, 56% yield).

$^1$H NMR (DMSO-d6, 300 MHz, 25° C.) δ 9.12 (s, 1H), 8.40 (d, 1H, J=6.0 Hz), 8.13 (m, 1H), 7.95 (m, 2H), 7.66 (m, 1H), 7.52 (m, 2H), 7.43 (m, 1H), 7.29 (m, 2H), 7.09 (m, 1H), 7.03 (m, 1H), 6.96 (dd, 1H, J=8.2, 2.2 Hz), 6.70 (m, 1H), 4.60 (m, 2H), 4.33 (m, 2H), 4.23 (m, 1H), 3.94 (m, 2H), 3.26 (m, 1H), 3.05 (m, 1H), 2.90 (m, 1H), 2.89 (m, 1H), 2.40 (m, 1H), 2.00 (m, 1H);

$^{13}$C NMR (DMSO-d6, 75 MHz, 25° C.) δ 165.73, 158.41, 151.98, 142.04, 141.41, 134.04, 133.47, 129.94, 129.51, 129.23, 129.09, 128.80, 128.31, 125.93, 122.76, 116.16, 115.40, 115.34, 115.30, 107.63, 65.90, 63.36, 57.38, 57.38, 51.87, 50.89, 29.89.

Figure 4:
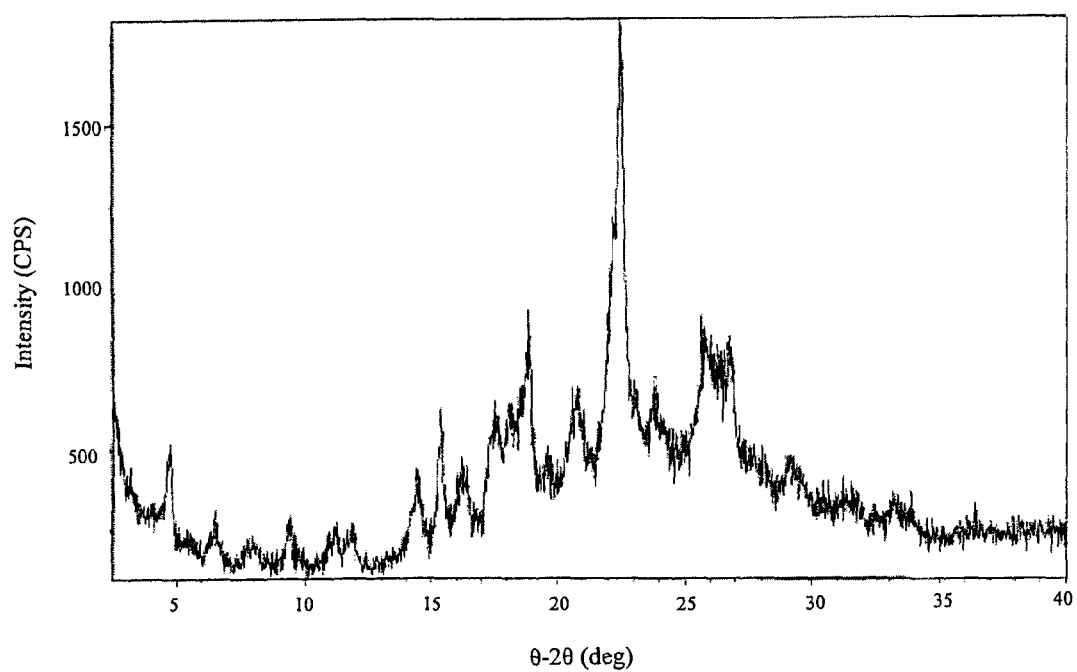
FIG. 4 shows the X-ray Powder Diffraction (XRPD) spectrogram for (R)-2-(3-((3-(isoquinolin-5-ylamino)pyrrolidin-1-yl)methyl)phenoxy)ethyl benzoate diphosphate, in a crystalline form.

The X-ray Powder Diffraction (XRPD) spectrogram for (R)-2-(3-((3-(isoquinolin-5-ylamino)pyrrolidin-1-yl)methyl)phenoxy)ethyl benzoate diphosphate is shown in FIG. 4.

Example 9

Preparation of (R)-2-(3-((3-(isoquinolin-5-ylamino) pyrrolidin-1-yl)methyl)phenoxy)ethyl Benzoate (Scheme 5, Step 4)

To a 100 mL round-bottomed flask with a magnetic stir bar were added (R)-N-(pyrrolidin-3-yl)isoquinolin-5-amine scuccinic acid salt (2.00 g, 6.04 mmol, from Example 5), tetrahydrofuran (30 mL), and 2-(3-formylphenoxy)ethyl benzoate (1.63 g, 6.04 mmol). The mixture was stirred at 20 to 25° C. for 15 minutes. To the mixture was added sodium triacetoxyborohydride (1.92 g, 9.05 mmol). The mixture was stirred at 20 to 25° C. for 20 hours. The reaction was quenched with 20 mL of 15% Na$_2$CO$_3$ (final pH ~10). Tetrahydrofuran was removed by distillation under vacuum. The residue was extracted with 30 mL of methyl tert-butyl ether. The organic layer was washed with 30 mL of water (twice) and concentrated under reduced pressure. The residue was purified by silica gel chromatography (0-12% methanol/dichloromethane) to give (R)-2-(3-((3-(isoquinolin-5-ylamino)pyrrolidin-1-yl)methyl)phenoxy)ethyl benzoate as a oil (2.57 g, 91% yield).

$^1$H NMR (CDCl$_3$, 300 MHz, 25° C.) δ 9.14 (s, 1H), 8.47 (d, 1H, J=6.0 Hz), 8.05 (m, 2H), 7.55 (m, 2H), 7.42 (m, 3H), 7.26 (m, 2H), 6.95 (m, 2H), 6.85 (m, 1H), 6.69 (d, 1H, J=7.5 Hz), 4.67 (m, 3H), 4.29 (m, 2H), 4.16 (m, 1H), 3.66 (s, 2H), 2.87 (m, 2H), 2.74 (m, 1H), 2.47 (m, 2H), 1.82 (m, 1H).

Example 10

Preparation of (R)-2-(3-((3-(isoquinolin-5-ylamino) pyrrolidin-1-yl)methyl)phenoxy)ethanol Hydrogen Chloride Salt (Scheme 5, Step 5)

To a 2 L flask equipped with an internal temperature probe and a mechanical stirrer were added 50 g of (R)-2-(3-((3-(isoquinolin-5-ylamino)pyrrolidin-1-yl)methyl)phenoxy) ethyl benzoate diphosphate (from Example 8), 300 mL of tetrahydrofuran and 380 mL of 2N sodium hydroxide. The resulting mixture was warmed to 38-42° C. and held for 24 hours. Upon disappearance of starting material the tetrahydrofuran was removed by distillation under vacuum. To the resulting mixture was added 860 mL of isopropyl acetate. After stirring for 20 minutes, the mixture was allowed to settle and the bottom aqueous layer was removed. The organic phase was then washed with water (2×570 mL). The resulting isopropyl acetate layer was azeotropically dried by distillation. To the remaining solution was slowly added 75.6 mL of ~1 HCl in isopropyl acetate. The resulting solid was then collected by filtration in an anhydrous environment and then washed with 3×220 mL of dry isopropyl acetate. The filter cake was dried in a vacuum oven for 18 hr, giving approximately 24.4 g (81% yield) of (R)-2-(3-((3-(isoquinolin-5-ylamino)pyrrolidin-1-yl)methyl)phenoxy)ethanol hydrochloride salt as a yellow solid.

$^1$H NMR (CD$_3$OD, 300 MHz, 25° C.) δ 9.21 (d, 1H, J=0.8 Hz), 8.40 (d, 1H, J=6.2 Hz), 8.24 (m, 1H), 7.60 (m, 1H), 7.51 (m, 1H), 7.38 (m, 1H), 7.18 (m, 1H), 7.12 (m, 1H), 7.05 (m, 1H), 6.94 (m, 1H), 4.54 (m, 1H), 4.46 (S, 2H), 4.06 (m, 2H), 3.87 (m, 2H), 3.80 (m, 1H), 3.69 (m, 1H), 3.53 (m, 2H), 2.65 (m, 1H), 2.34 (m, 1H);

$^{13}$C NMR (CD$_3$OD, 75 MHz, 25° C.) δ 161.11, 152.00, 143.24, 139.33, 133.25, 131.62, 130.84, 130.62, 128.87, 123.90, 118.51, 118.09, 117.65, 117.50, 111.42, 70.91, 61.71, 59.82, 59.43, 53.99, 52.75, 31.40.

Example 11

Preparation of (R)-2-(3-((3-(isoquinolin-5-ylamino) pyrrolidin-1-yl)methyl)phenoxy)ethanol 2,5-dihydroxybenzoic Acid Salt (Scheme 5, Step 5)

To a 500 mL flask equipped with an internal temperature probe and a mechanical stirrer were added 50 g of (R)-2-(3-((3-(isoquinolin-5-ylamino)pyrrolidin-1-yl)methyl)phenoxy)ethyl benzoate diphosphate (from Example 8), 72 mL of tetrahydrofuran and 90 mL of 2 N sodium hydroxide. The resulting mixture was warmed to 38-42° C. and held for 24 hours. Upon disappearance of starting material the tetrahydrofuran was removed by rotary evaporation. The resulting mixture was extracted with 200 ml of isopropyl acetate and washed with water (2×135 mL). The organic layer was concentrated and the residue was azeotropically dried by repeated rotary evaporation with isopropyl acetate. Crude product of (R)-2-(3-((3-(isoquinolin-5-ylamino)pyrrolidin-1-yl)methyl)phenoxy)ethanol was isolated as a foamy solid (6.5 g, 99% yield). Crude (R)-2-(3-((3-(isoquinolin-5-ylamino)pyrrolidin-1-yl)methyl)phenoxy)ethanol (2.0 g, 5.5 mmol) was combined with 55 mL of a 0.1 M solution of 2,5-dihydroxybenzoic acid in ethanol. The mixture was gently heated to ~50° C. with stirring to give a solution. The solution was cooled to ~22° C. and the slurry was stirred for 2 hours and the solid was isolated by filtration. Approximately 2.15 g of the (R)-2-(3-((3-(isoquinolin-5-ylamino) pyrrolidin-1-yl)methyl)phenoxy)ethanol 2,5-dihydroxybenzoic acid salt was obtained as a solid (80% yield).

$^1$H NMR (CD$_3$OD, 300 MHz) δ 9.06 (s, 1H), 8.29 (d, J=6.1 Hz, 1H), 7.98 (d, J=6.1 Hz, 1H), 7.50 (t, J=8.0 Hz, 1H), 7.40 (d, J=8.0 Hz, 1H), 7.36-7.29 (m, 2H), 7.13-6.97 (m, 3H), 6.85-6.79 (m, 2H), 6.67 (d, J=9.0 Hz, 1H), 4.51-4.40 (m, 1H), 4.30 (s, 2H), 4.02-3.95 (m, 2H), 3.84-3.77 (m, 2H), 3.67-3.50 (m, 2H), 3.46-3.32 (m, 2H), 2.70-2.55 (m, 1H), 2.30-2.15 (m, 1H);

$^{13}$C NMR (CD$_3$OD, 75 MHz) δ 174.59, 159.80, 154.56, 151.87, 148.82, 141.89, 140.42, 133.20, 130.13, 129.81, 128.51, 127.17, 122.42, 120.86, 118.04, 116.69, 116.54, 116.01, 115.82, 115.73, 115.34, 108.99, 69.48, 60.39, 58.84, 58.47, 52.59, 51.60, 30.39.

Figure 5:
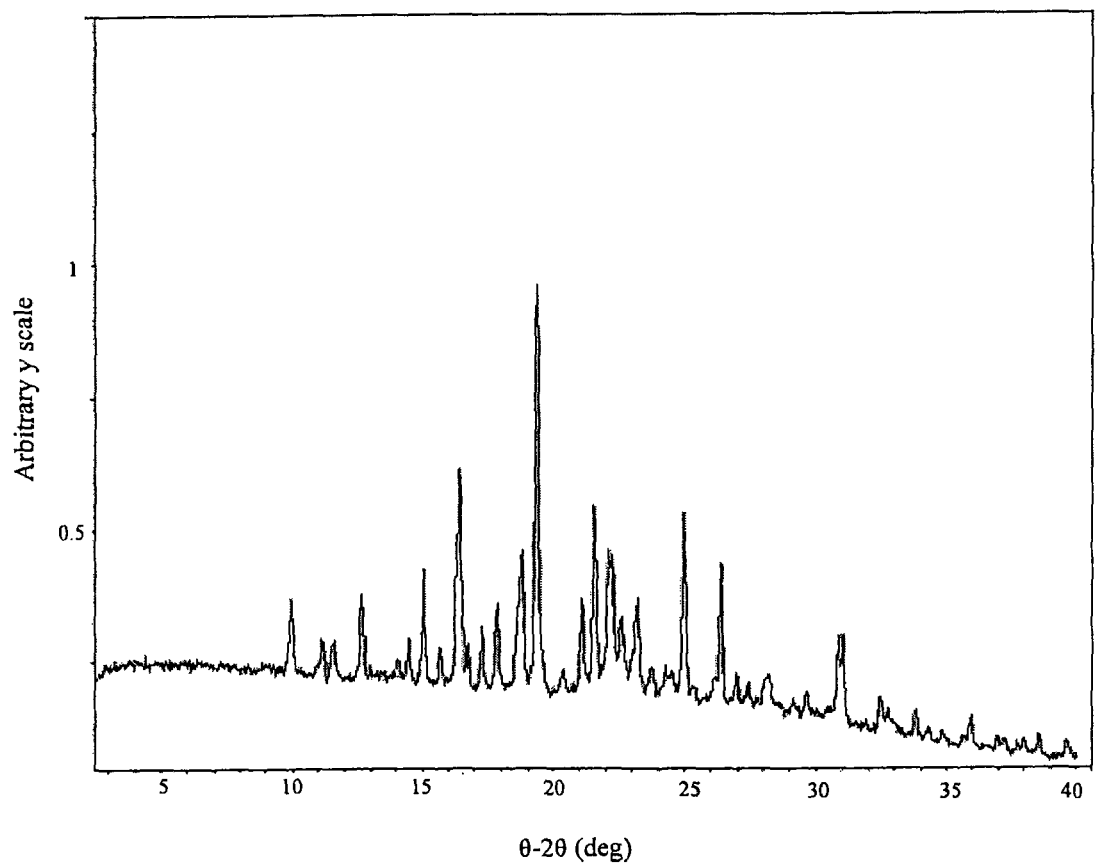
FIG. 5 shows the X-ray Powder Diffraction (XRPD) spectrogram for (R)-2-(3-((3-(isoquinolin-5-ylamino)pyrrolidin-1-yl)methyl)phenoxy)ethanol 2,5-dihydroxybenzoic acid salt, in a crystalline form.

The X-ray Powder Diffraction (XRPD) spectrogram for (R)-2-(3-((3-(isoquinolin-5-ylamino)pyrrolidin-1-yl)methyl)phenoxy)ethanol 2,5-dihydroxybenzoic acid salt is shown in FIG. 5.

Example 12

Preparation of (R)-2-(3-((3-(isoquinolin-5-ylamino)pyrrolidin-1-yl)methyl)phenoxy)ethanol L-tartaric Acid Salt (Scheme 5, Step 5)

Crude (R)-2-(3-((3-(isoquinolin-5-ylamino)pyrrolidin-1-yl)methyl)phenoxy)ethanol (1.0 g, 2.7 mmol, from example 11) was dissolved in 11 mL of ethanol. The solution was stirred while 27.5 mL of a 0.1 M solution of L-tartaric acid in ethanol was added. After 2 hours, the resulting suspension was filtered, washed with ethanol, and dried under nitrogen. Approximately 1.1 g of (R)-2-(3-((3-(isoquinolin-5-ylamino)pyrrolidin-1-yl)methyl)phenoxy)ethanol L-tartaric acid salt was isolated as a yellow solid (79% yield).

$^1$H NMR (CD$_3$OD, 300 MHz) δ 9.09 (s, 1H), 8.37 (d, J=7.2 Hz, 1H), 8.02 (d, J=7.2 Hz, 1H), 7.52 (t, J=8.0 Hz, 1H), 7.43 (d, J=8.0 Hz, 1H), 7.35 (t, J=8.0 Hz, 1H), 7.12-6.99 (m, 3H), 6.83 (d, J=7.5 Hz, 1H), 4.51-4.42 (m, 3H), 4.33 (s, 2H), 4.06-3.99 (m, 2H), 3.88-3.81 (m, 2H), 3.74-3.64 (m, 1H), 3.63-3.51 (m, 1H), 3.45-3.34 (m, 2H), 2.70-2.56 (m, 1H), 2.31-2.17 (m, 1H).

Example 13

Preparation of 2-(3-formylphenoxy)ethyl Benzoate (Scheme 5, Step 6)

To a 5 L flask equipped with an internal temperature probe and a mechanical stirrer was added dimethyl sulfoxide (500 mL), 3-hydroxybenzaldehyde (100.0 g, 0.819 mol), ethylene carbonate (108 g, 1.23 mol), and potassium carbonate (136 g, 0.983 mol). The resulting mixture was stirred at 110 to 125° C. until all 3-hydroxybenzaldehyde starting material was consumed. (Additional portions of ethylene carbonate may be added to drive the reaction to completion). The reaction mixture was then cooled to below 25° C. and diluted with isopropyl acetate (1.0 L) and water (1.5 L). The mixture was stirred until the residual potassium carbonate was completely dissolved. The layers were separated and the organic layer was washed with an additional portion of water (1.5 L). Additional isopropyl acetate was added (1.0 L), and then distilled off to leave a final volume of ~1 L of dry organic solution of 3-(2-hydroxyethoxy)benzaldehyde.

The resulting solution of 3-(2-hydroxyethoxy)benzaldehyde was cooled to 60° C. Triethylamine (204 mL, 1.46 mol) and benzoic anhydride (139 g, 0.614 mol) were added. The solution was stirred at 75 to 85° C. until less than 0.5% 3-(2-hydroxyethoxy)benzaldehyde remaining (additional benzoic anhydride can be added to progress the reaction to completion). The reaction was cooled to 20 to 40° C. Water (1.5 L) was added to quench the reaction. The layers were separated, and the organic layer was washed with dilute acid (1.0 L of 0.1 N HCl) and water (1.0 L). The resulting organic solution was concentrated to give a final volume of 200 mL. The solution was then cooled to 0 to 10° C., and 1% seed crystals were added to induce crystallization. Heptane (100 mL) was then slowly added and the mixture was stirred at 0-5° C. for 1 hr. The resulting solid was isolated by filtration and washed with 100 mL of a 1:1 isopropyl acetate/heptane. The cake was then dried under vacuum for 3 hr to give approximately 71.9 g (33% yield) of 2-(3-formylphenoxy)ethyl benzoate as an off-white solid.

$^1$H NMR (CD$_3$OD, 300 MHz, 25° C.) δ 9.94 (s, 1H), 8.01 (m, 2H), 7.59 (m, 1H), 7.51 (m, 1H), 7.51 (m, 1H), 7.49 (m, 1H), 7.47 (m, 1H), 7.30 (m, 1H), 4.68 (m, 1H), 4.42 (m, 1H); $^{13}$C NMR (CD$_3$OD, 75 MHz, 60° C.) δ 193.95, 139.53, 114.88, 160.83, 122.90, 131.50, 124.37, 67.62, 64.72, 167.94, 31.26, 130.71, 129.69, 134.46.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

What is claimed is:

1. A process for preparing a compound of Formula VII or its salt, comprising the steps of:
   (a) reacting a Formula I compound, a Formula II compound, an acid having pKa<5, with a reducing agent to form a compound of Formula III;

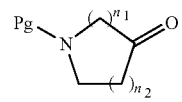

Formula I

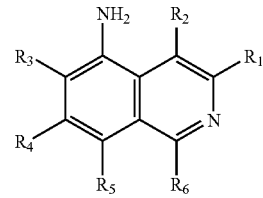

Formula II

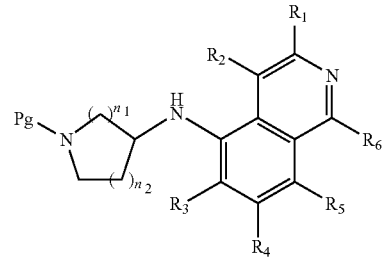

Formula III wherein Pg is a protecting group;
$n_1$ is 1;
$n_2$ is 1 or 2;
provided when $n_1$ is 2, $n_2$ is 2 or 3; and
$R_1$, $R_2$, $R_3$, $R_4$, $R_5$, and $R_6$ are independently hydrogen, halo, alkyl, alkenyl, alkynyl, amino, alkylamino, alkenylamino, alkynylamino, hydroxyl, alkoxy, alkenoxy, or alkynoxy;
   (b) reacting the compound of Formula III with an acidic chiral resolving agent to form a diastereomeric salt depicted as Formula IV;

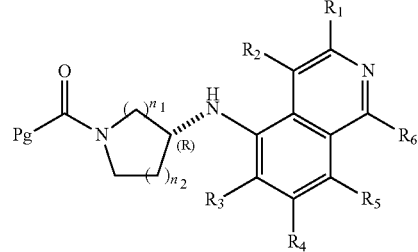

Formula IV

Chiral Resolving Agent (c) reacting the diastereomeric salt with a basic aqueous solution to remove the acidic chiral resolving agent and then removing the protecting group under the deprotection conditions to form a compound of Formula V;

Formula V

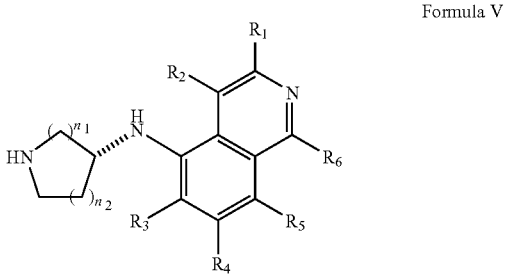

(d) reacting the compound of Formula V with a compound of Formula VI to form a compound of Formula VII;

Formula VI

Formula VII

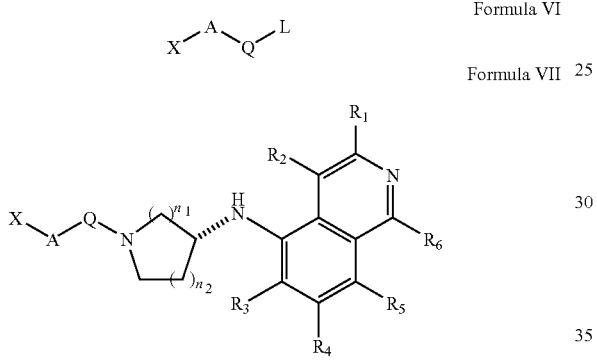

wherein $R_1$-$R_6$, $n_1$ and $n_2$ are the same as described above;
A is aryl or heteroaryl;
X is from 0 to 5 substituents on A, and is selected from the group consisting of: hydroxy, oxo, nitro, methoxy, ethoxy, alkoxy, substituted alkoxy, trifluoromethoxy, haloalkoxy, fluoro, chloro, bromo, iodo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, ureido, substituted ureido, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl;
Q is —$CH_2$—, —$CH_2CH_2$—, or absent; and
L is CHO, chloro, bromo, iodo, or O—$SO_2$—$R_7$; wherein $R_7$ is methyl, ethyl, $CF_3$, p-tolyl, phenyl, or p-nitrophenyl.

2. The process according to claim 1, wherein said acidic chiral resolving agent is (R)- or (S)-enantiomer of tartaric acid, (R)- or (S)-enantiomer of dibenzoyltartaric acid, (R)- or (S)-enantiomer of di-p-toluoyltartaric acid, (R)- or (S)-enantiomer of camphor-10-sulfonic acid, or (R)- or (S)-enantiomer of mandelic acid.

3. A process for preparing a compound of Formula VII or its salt, comprising the steps of:

(a) reacting a Formula I compound and a Formula II compound with a reducing agent to form a compound of Formula III;

Formula I

Formula II

Formula III

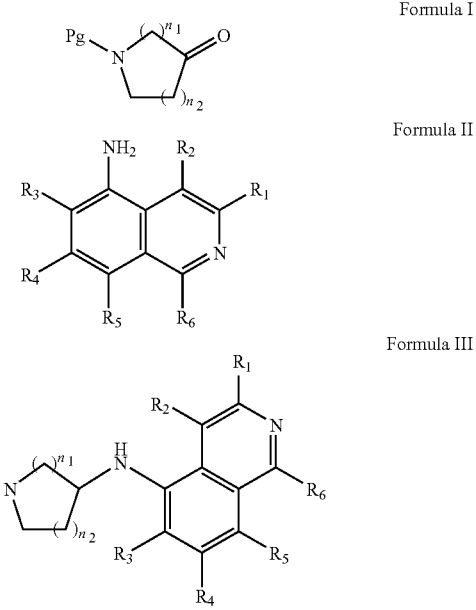

wherein Pg is a protecting group;
$n_1$ is 1 or 2;
$n_2$ is 1, 2 or 3;
provided when $n_1$ is 2, $n_2$ is 2 or 3; and
$R_1$, $R_2$, $R_3$, $R_4$, $R_5$, and $R_6$ are independently hydrogen, halo, alkyl, alkenyl, alkynyl, amino, alkylamino, alkenylamino, alkynylamino, hydroxyl, alkoxy, alkenoxy, or alkynoxy;

(b) removing the protecting group from the Formula III compound under the deprotection conditions to form a compound of Formula VIII;

Formula VIII

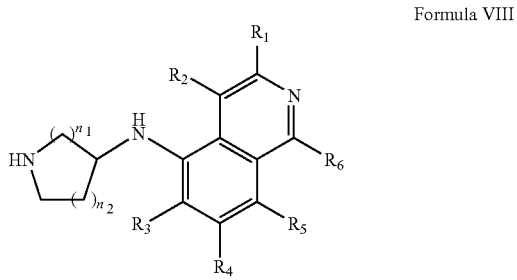

(c) reacting the compound of Formula VIII with a compound of Formula VI to form a compound of Formula IX;

Formula VI

-continued

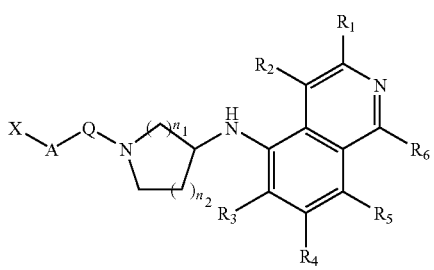

Formula IX wherein $R_1$-$R_6$, $n_1$ and $n_2$ are the same as described above;
A is a aryl or heteroaryl;
X is from 0 to 5 substituents on A, and is selected from the group consisting of: hydroxy, oxo, nitro, methoxy, ethoxy, alkoxy, substituted alkoxy, trifluoromethoxy, haloalkoxy, fluoro, chloro, bromo, iodo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, ureido, substituted ureido, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl;
Q is —$CH_2$—, —$CH_2CH_2$—, or absent; and
L is CHO, chloro, bromo, iodo, or O—$SO_2$—$R_7$; wherein $R_7$ is methyl, ethyl, $CF_3$, p-tolyl, phenyl, or p-nitrophenyl;

(d) reacting the compound of Formula IX with an acidic chiral resolving agent to form a diastereomeric salt depicted as Formula X;

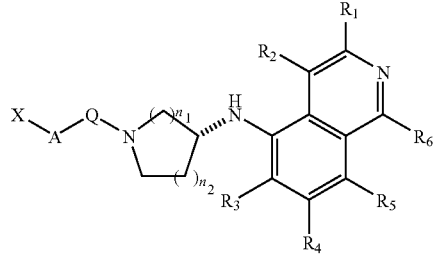

Formula X

· Acidic Chiral Resolving Agent (e) reacting the diastereomeric salt with a basic aqueous solution to remove the acidic chiral resolving agent to form a compound of Formula VII,

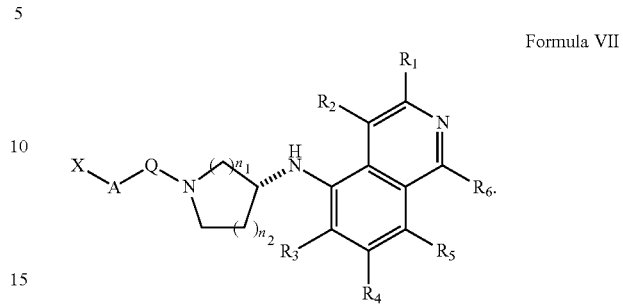

Formula VII

4. The process according to claim 3, wherein said acidic chiral resolving agent is (R)- or (S)-enantiomer of tartaric acid, (R)- or (S)-enantiomer of dibenzoyltartaric acid, (R)- or (S)-enantiomer of di-p-toluoyltartaric acid, (R)- or (S)-enantiomer of camphor-10-sulfonic acid, or (R)- or (S)-enantiomer of mandelic acid.

5. The process of claim 2, wherein the acidic chiral resolving agent is (R)-enantiomer of tartaric acid.

6. The process of claim 2, wherein the acidic chiral resolving agent is (R)-enantiomer of dibenzoyltartaric acid.

7. The process of claim 1, wherein step (b), the protecting group is t-butylcarbamoyl, and the protecting group is removed by treating with an acid.

8. The process of claim 1, wherein step (b), the protecting group is benzyl or benzylcarbamoyl, and the protecting group is removed by hydrogenolysis.

9. The process of claim 1, wherein step (d), L is CHO, and the compound of Formula VII is formed by reductive amination.

10. The process of claim 1, wherein step (d), L is chloro, bromo, iodo, or O—$SO_2$—$R_7$, and the compound of Formula VII is formed by alkylation.

11. The process of claim 1, wherein A is aryl.

12. The process of claim 1, wherein $n_1$ is 1 and $n_2$ is 1.

13. The process of claim 1, wherein the Formula VII compound is

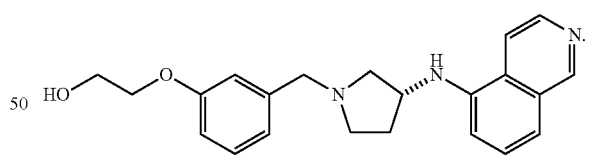

* * * * *